United States Patent [19]

Sprecker et al.

[11] Patent Number: 5,030,618
[45] Date of Patent: Jul. 9, 1991

[54] ALKYL-SUBSTITUTED TETRA- OR HEXAHYDROBENZOPYRAN DERIVATIVES, ORGANOLEPTIC USES THEREOF AND PROCESS FOR PREPARING SAME

[75] Inventors: Mark A. Sprecker, Sea Bright; Robert P. Belko, Woodbridge; Marie R. Hanna, Keyport; Charles E. J. Beck, Summit; Salvatore M. Brucato, Carteret, all of N.J.

[73] Assignee: International Flavors and Fragrances Inc., New York, N.Y.

[21] Appl. No.: 545,625

[22] Filed: Jun. 29, 1990

Related U.S. Application Data

[62] Division of Ser. No. 497,693, Mar. 22, 1990, Pat. No. 4,999,439.

[51] Int. Cl.$^5$ .............................................. A61K 7/46
[52] U.S. Cl. .................................................... 512/13
[58] Field of Search .......................................... 512/13

[56] References Cited

U.S. PATENT DOCUMENTS

| | | | |
|---|---|---|---|
| 3,901,924 | 8/1975 | Auger et al. | 260/345 |
| 3,951,875 | 4/1976 | Auger et al. | 252/522 |
| 4,224,176 | 9/1980 | Sprecker et al. | 512/13 |
| 4,233,226 | 11/1980 | Takeda et al. | 512/13 |
| 4,438,023 | 3/1984 | Skorianetz et al. | 512/13 |
| 4,608,193 | 8/1986 | Sprecker et al. | 512/13 |

FOREIGN PATENT DOCUMENTS

| | | | |
|---|---|---|---|
| 2305981 | 8/1973 | Fed. Rep. of Germany | 549/330 |
| 047389 | 12/1970 | Japan . | |
| 468411 | 11/1975 | U.S.S.R. | 549/401 |
| 618374 | 8/1978 | U.S.S.R. . | |
| 620487 | 8/1978 | U.S.S.R. . | |
| 638597 | 12/1978 | U.S.S.R. . | |

OTHER PUBLICATIONS

Arctander, "Perfume and Flavor Chemicals (Aroma Chemicals)", 1969, Monograph 2926, "Tetrahydro Pyranyl Cortonate".

Arctander, "Perfume and Flavor Chemicals (Aroma Chemicals)", 1969, Monograph 1935, "5-Methyl-3-Butyl-Tetrahydropyran-4-yl Acetate".

Arctander "Perfume and Flavor Chemicals (Aroma Chemicals)", Vol. I, 1969, Monograph 1053.

*Primary Examiner*—James H. Reamer
*Attorney, Agent, or Firm*—Arthur L. Liberman

[57] ABSTRACT

Described are alkyl-substituted tetra- or hexahydrobenzopyran derivatives defined according to one of the generic structures:

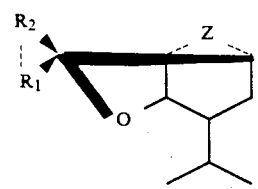

or

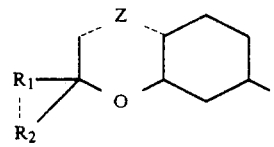

wherein Z is a moiety in the alternative either

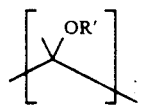

or

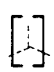

wherein in the moiety having the structure:

(Abstract continued on next page.)

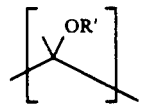

R' is methyl or ethyl and in the moiety having the structure:

one of the dashed lines is a carbon-carbon double bond and each of the other of the dashed lines represent carbon-carbon single bonds; wherein $R_1$ and $R_2$ taken separately represent hydrogen or $C_1$–$C_3$ lower alkyl (with the proviso that $R_1$ and $R_2$ are not both hydrogen) or $R_1$ and $R_2$ taken together complete a $C_5$ or $C_6$ cycloalkyl moiety; and uses thereof in augmenting or enhancing the aroma of perfume compositions, colognes and perfumed articles including but not limited to solid or liquid anionic, cationic, nonionic or zwitterionic detergents, fabric softener compositions, fabric softener articles, hair preparations, cosmetic powders and perfumed polymers. Also described are synthesis processes for preparing such alkyl-substituted tetra- or hexahydrobenzopyran derivatives by means of reacting isopulegol or an isomer thereof with an acetal or ketal.

8 Claims, 18 Drawing Sheets

GLC PROFILE FOR EXAMPLE I.

FIG. 2 NMR SPECTRUM FOR EXAMPLE I.

GLC PROFILE FOR EXAMPLE II.

NMR SPECTRUM FOR EXAMPLE II, PEAK 31 OF FIG. 3.

GLC PROFILE FOR EXAMPLE III.

FIG. 7 NMR SPECTRUM FOR EXAMPLE III, FRACTION 15.

FIG.8 NMR SPECTRUM FOR EXAMPLE III, FRACTION 7.

GLC PROFILE FOR EXAMPLE IV.

GLC PROFILE FOR EXAMPLE V.

NMR SPECTRUM FOR EXAMPLE V, PEAKS 122, 123 AND 124 OF FIG. 12.

GLC PROFILE FOR EXAMPLE VI.

NMR SPECTRUM FOR EXAMPLE VI, PEAKS 152, 153 AND 154 OF FIG. 15.

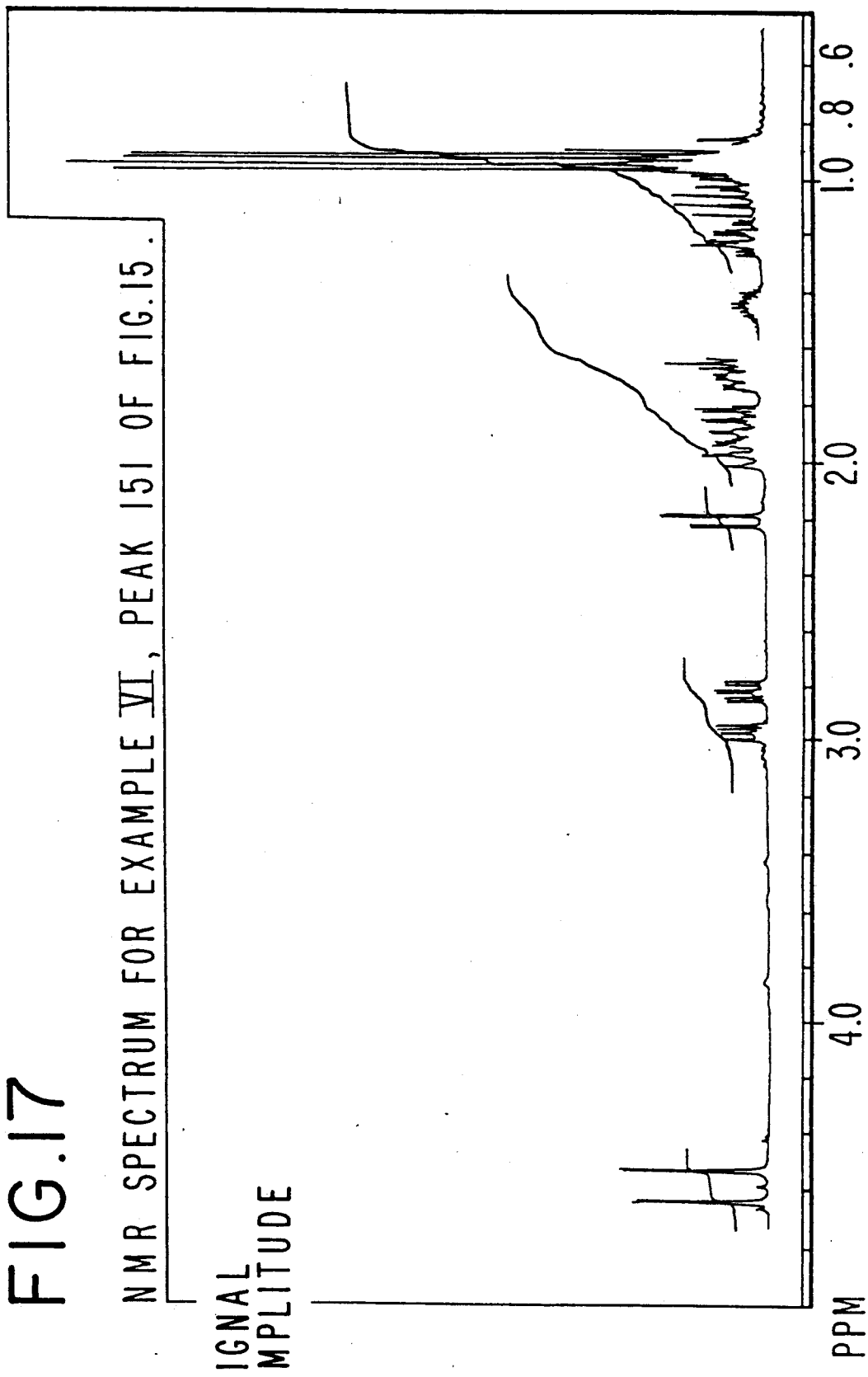

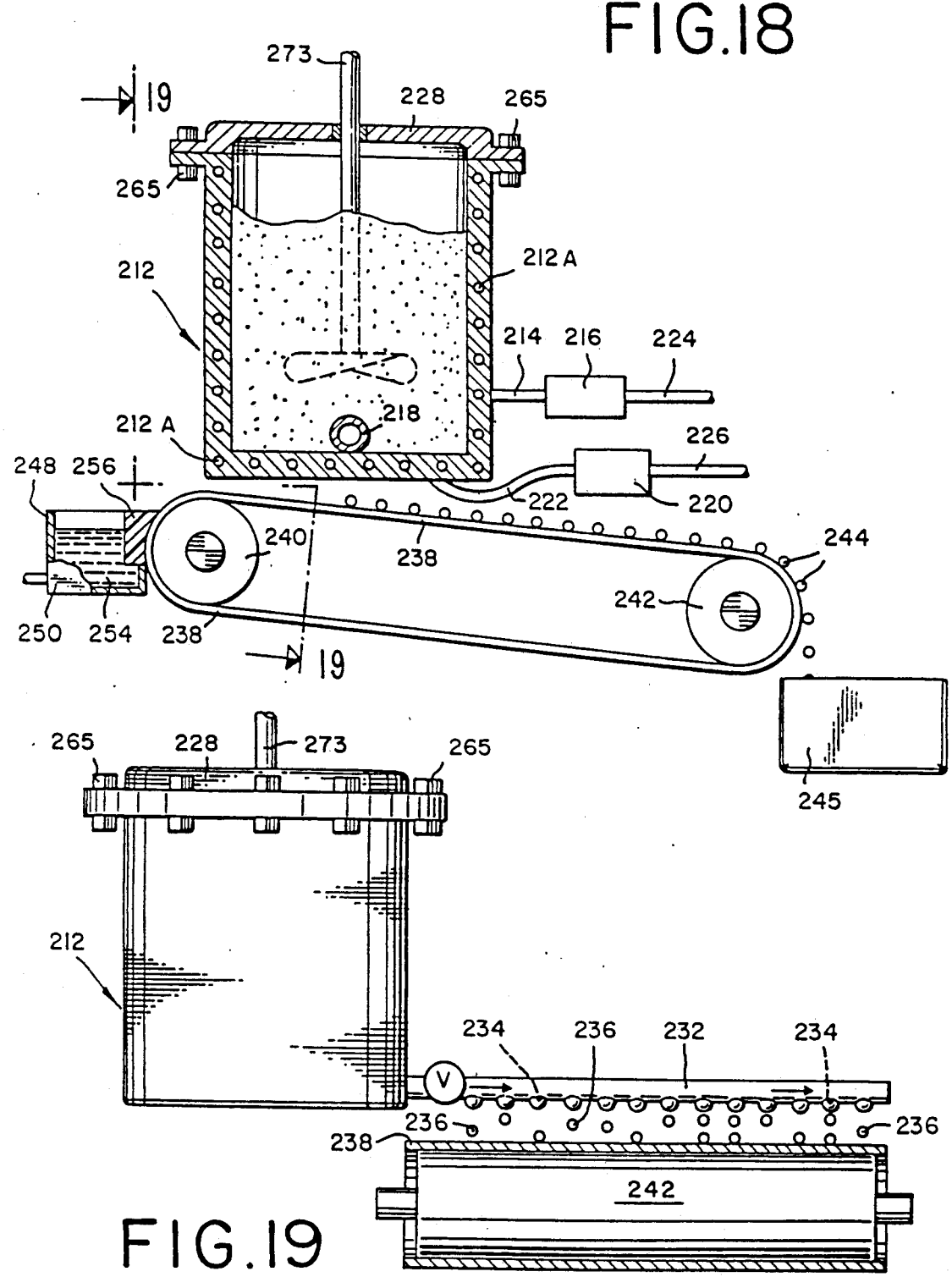

ALKYL-SUBSTITUTED TETRA- OR HEXAHYDROBENZOPYRAN DERIVATIVES, ORGANOLEPTIC USES THEREOF AND PROCESS FOR PREPARING SAME

This is a divisional of application Ser. No. 497,693, filed 3/22/90, U.S. Pat. No. 4,999,439, issue 3/12/91.

BACKGROUND OF THE INVENTION

Described are alkyl-substituted tetra- or hexahydrobenzopyran derivatives defined to one of the structures:

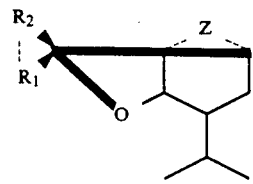

or

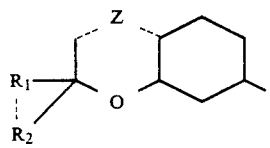

wherein Z is in the alternative one of the moieties:

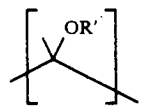

or

wherein in the moiety:

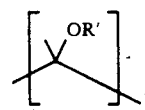

R' is methyl or ethyl and in the moiety:

one of the dashed lines is a carbon-carbon double bond and each of the other of the dashed lines represent carbon-carbon single bonds; wherein $R_1$ and $R_2$ taken separately are hydrogen or $C_1$–$C_3$ lower alkyl or $R_1$ and $R_2$ taken together complete a $C_5$ or $C_6$ cycloalkyl moiety as well as organoleptic uses thereof in augmenting or enhancing the aroma of perfume compositions, colognes or perfumed articles.

There has been considerable work performed relating to substances which can be used to impart (alter, modify or enhance) fragrances to (or in) various consumable materials. These substances are used to diminish the use of natural materials some of which may be in short supply and to provide more uniform properties in the finished product.

Floral, magnolia, fruity, citrusy, peach, natural liatrix-like, green, hay-like, lactonic sweet, coumarin-like, coconut-like, buttery, jasmine, minty, dry and woody aromas with green, herbaceous, coriander seed-like, fruity, peach, celery-like, jasmine and lactonic undertones and citrusy, orange-peel-like, minty, herbaceous and buttery topnotes are highly desirable in several types of perfume compositions and for use in perfumed articles.

Arctander "Perfume and Flavor Chemicals (Aroma Chemicals)", Volume I, 1969, at Monograph 1053 discloses the use of the compound having the structure:

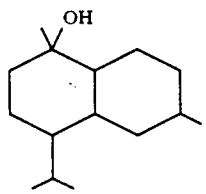

in augmenting or enhancing the aroma of perfume compositions. This material, commonly known as dihydrocadinol is disclosed to have a powerful and very dry, musty, woody odor of similarity to the dry notes of ambergris. As indicated that it can be used to give a "lift" to a number of non-floral fragrance types and in combination with galbanum, oakmoss and the like it may form a very important part of certain types of luxury perfume. The compound having the structure:

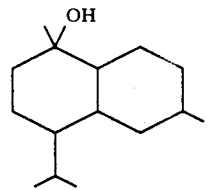

is difficult to synthesize and relatively expensive. In addition, the compounds of our invention have nuances distinctly advantageous over the compound having the structure:

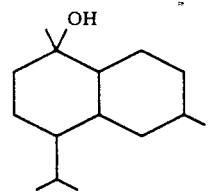

and have even a greater strength, tenacity and substantivity.

[Structure drawing]

[Structure drawing]

[Structure drawing]

and

[Structure drawing with OH]

(Conditions: SE-30 column programmed at 200° C. isothermal).

Figure 2:
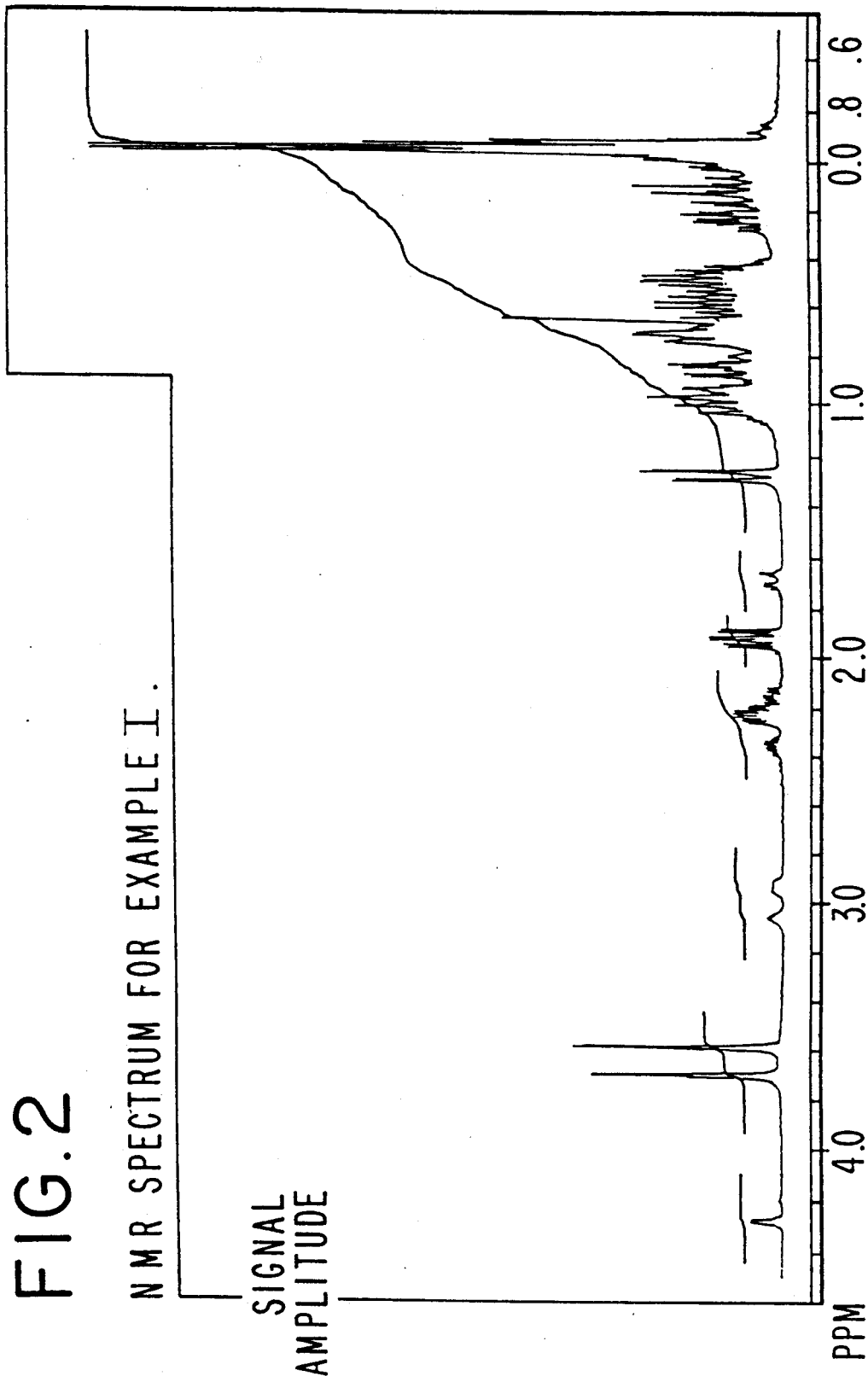

FIG. 2 is the NMR spectrum for the mixture of having the structure:

[Structure drawing]

wherein one of the dashed lines in each of the compounds of the mixture represents a carbon-carbon double bond and each of the other of the dashed lines represent carbon-carbon single bonds.

Figure 3:
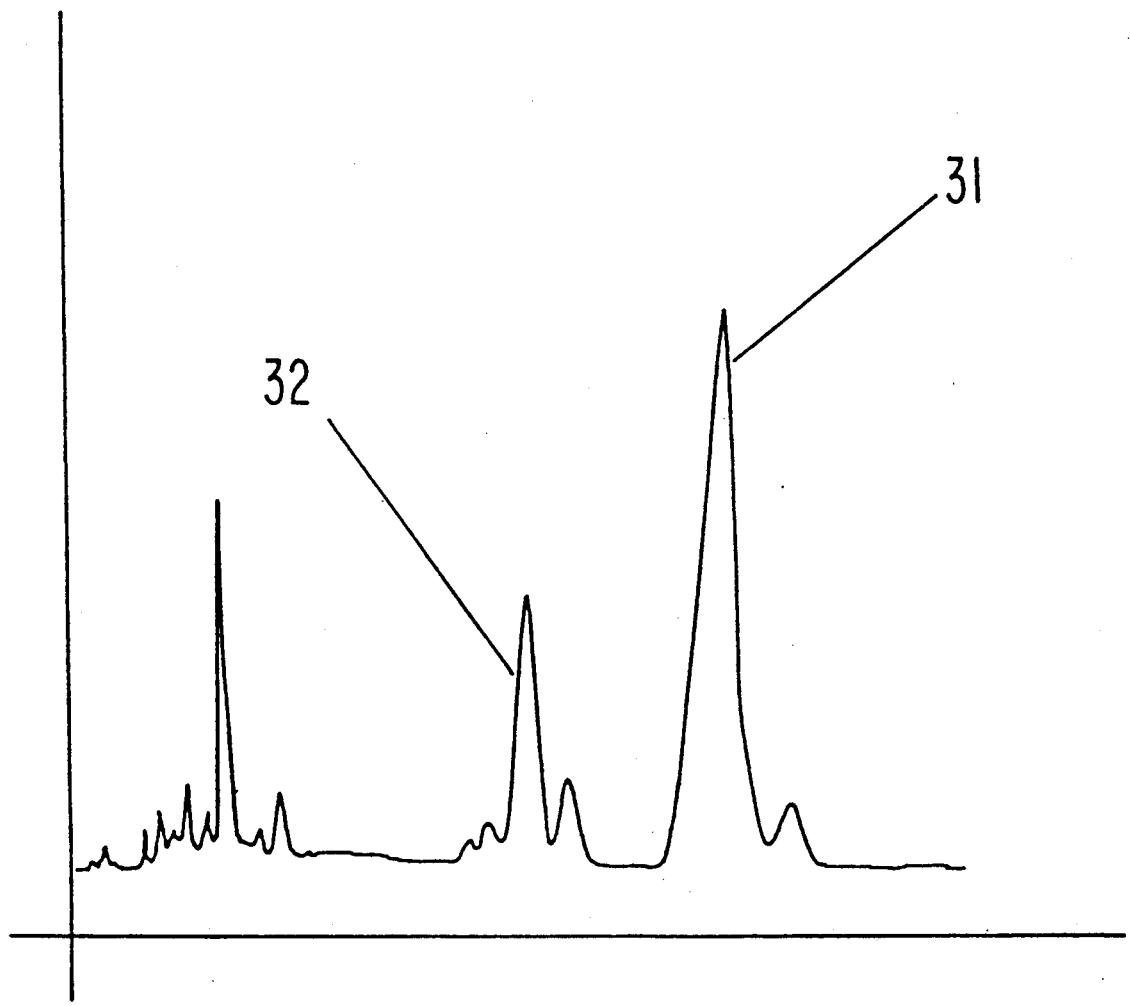

FIG. 3 is the GLC profile for the reaction product of Example II containing the compounds having the structures:

[Structure drawing with OCH₃]

[Structure drawing]

and

[Structure drawing]

-continued

[Structure drawing]

Figure 4:
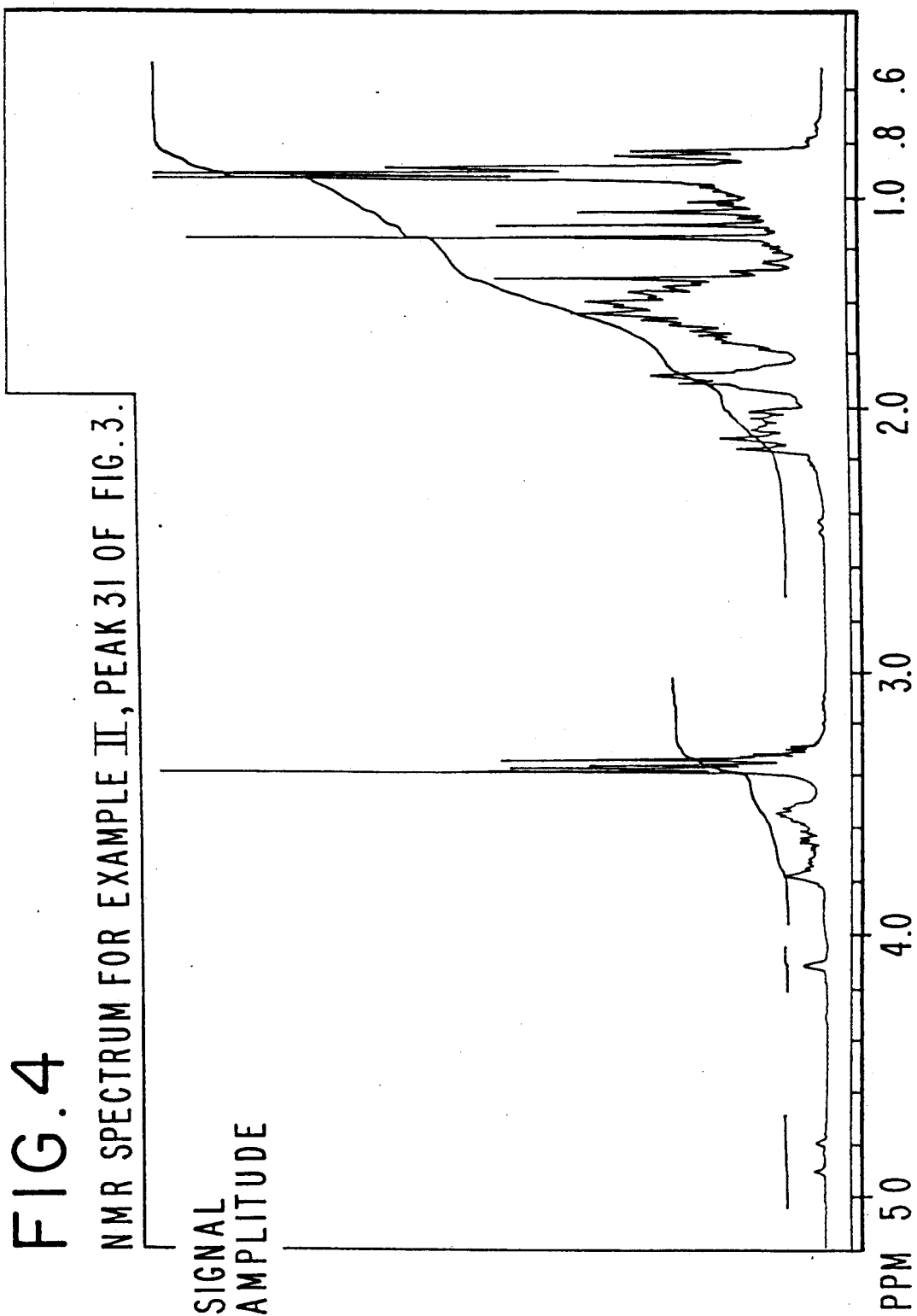

FIG. 4 is the NMR spectrum for the peak indicated by reference numeral 31 of FIG. 3, the GLC profile and is for the compound having the structure:

[Structure drawing with OCH₃]

synthesized according to Example II.

Figure 5:
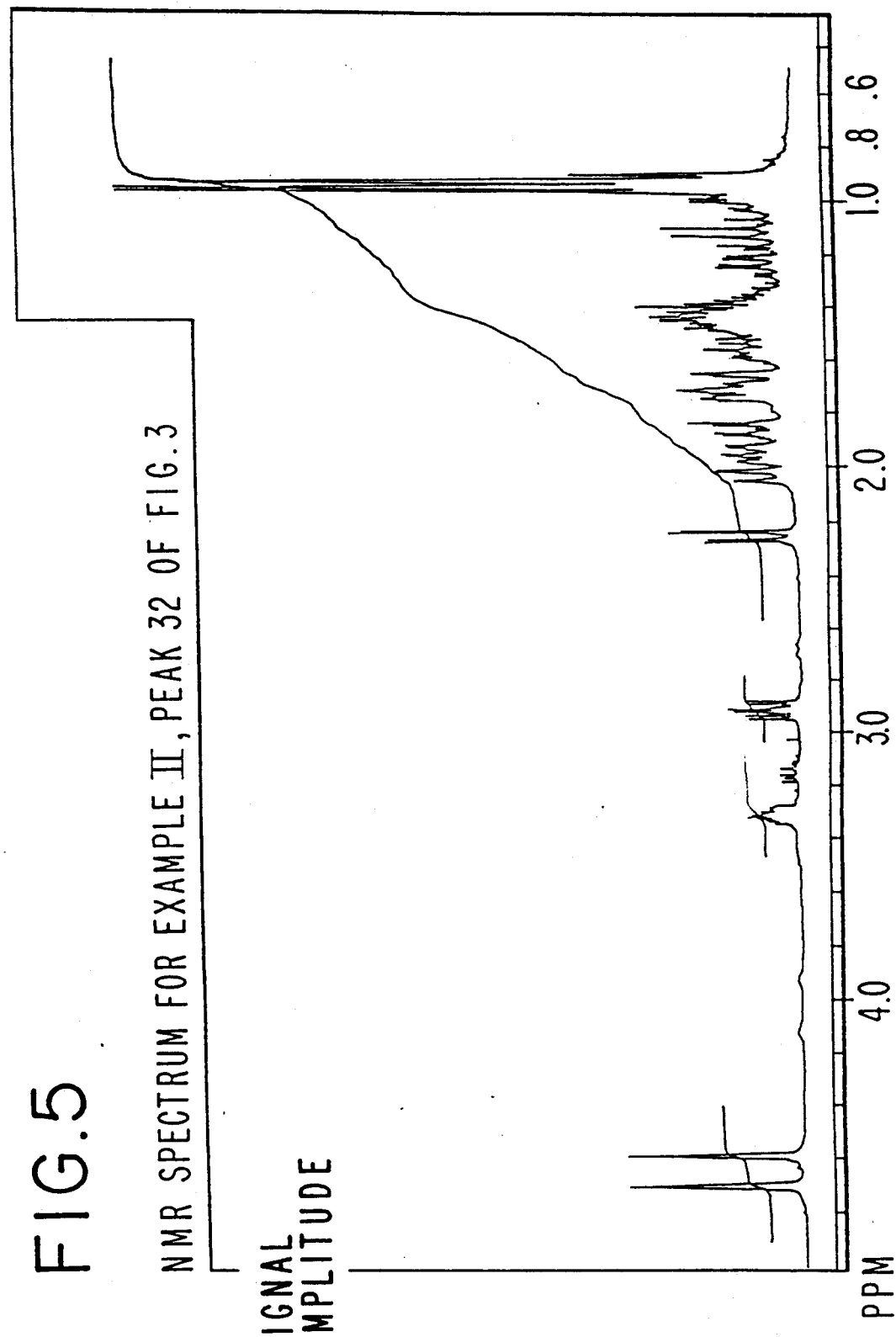

FIG. 5 is the NMR spectrum of the peak indicated by reference numeral 32 of the GLC profile of FIG. 3 and is for the compound having the structure:

[Structure drawing]

synthesized according to Example II.

Figure 6:
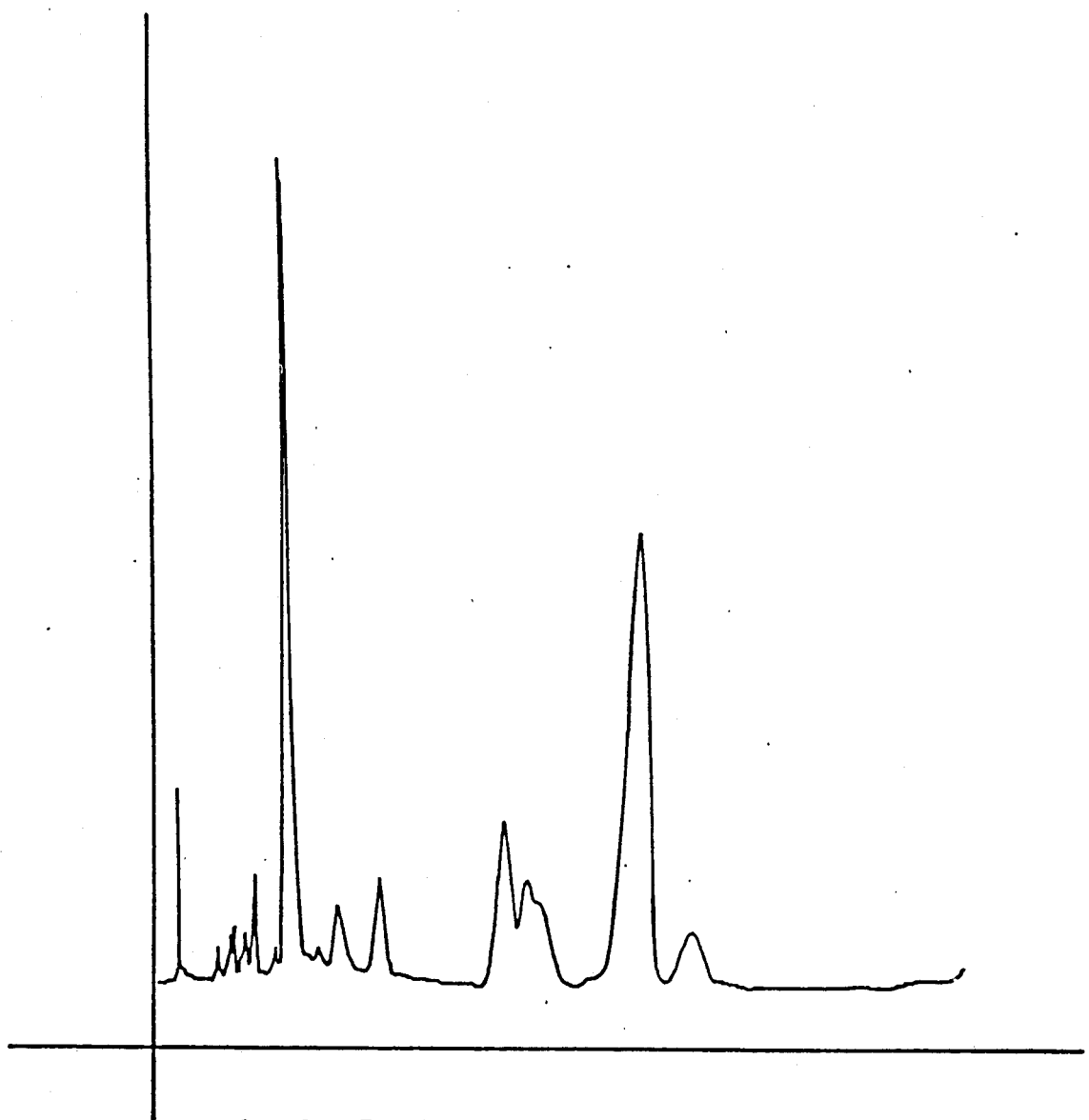

FIG. 6 is the GLC profile for the reaction product of Example III containing the compounds having the structures:

[Structure drawing with OCH₃]

[Structure drawing]

[Structure drawing]

and

[Structure drawing]

(Conditions: SE-30 column programmed at 180° C. isothermal).

Figure 7:
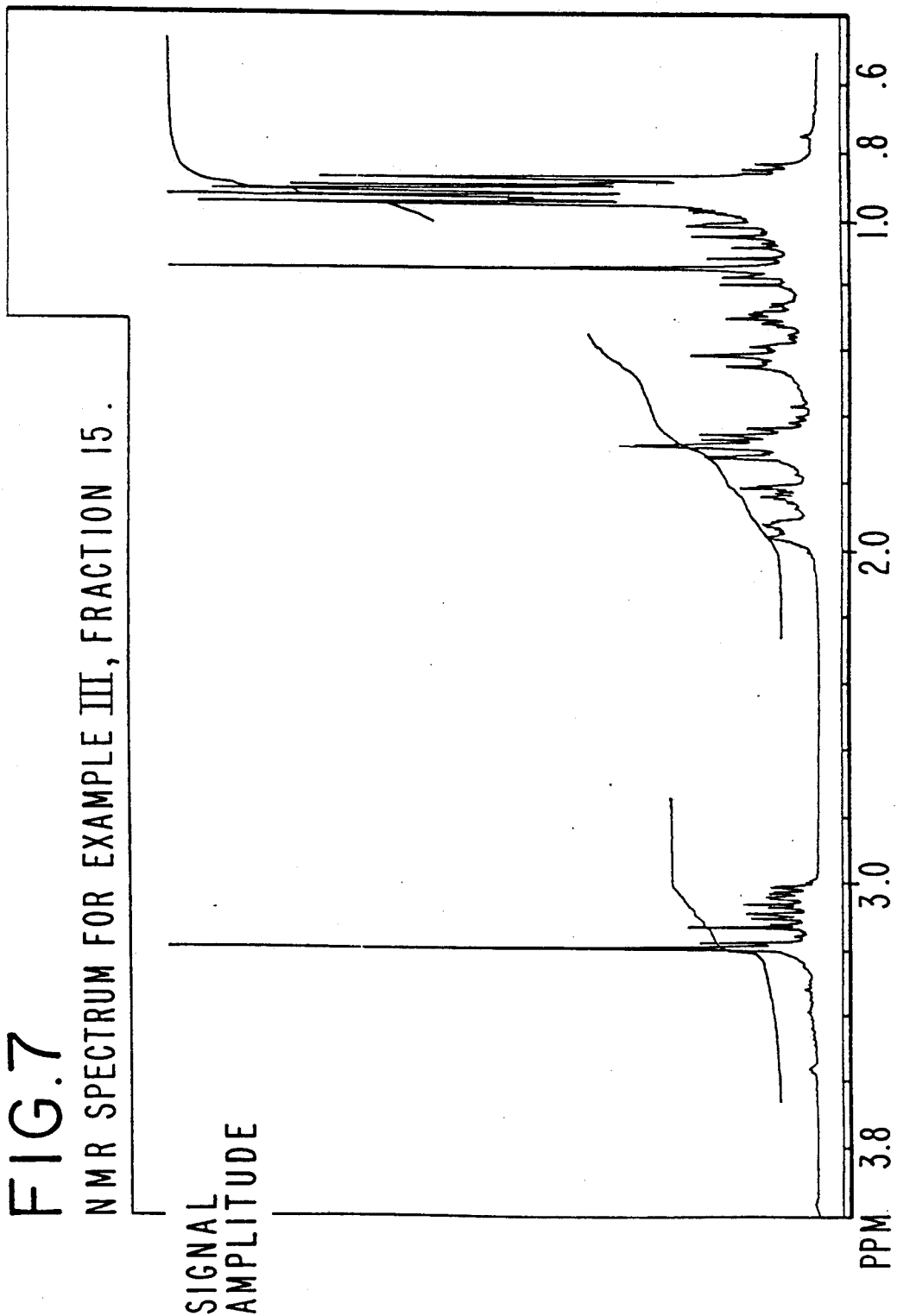

FIG. 7 is the NMR spectrum for distillation fraction 15 of the distillation of the reaction product of Example III for the compound having the structure:

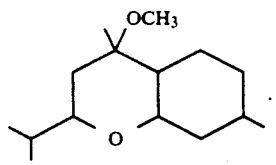

Figure 8:
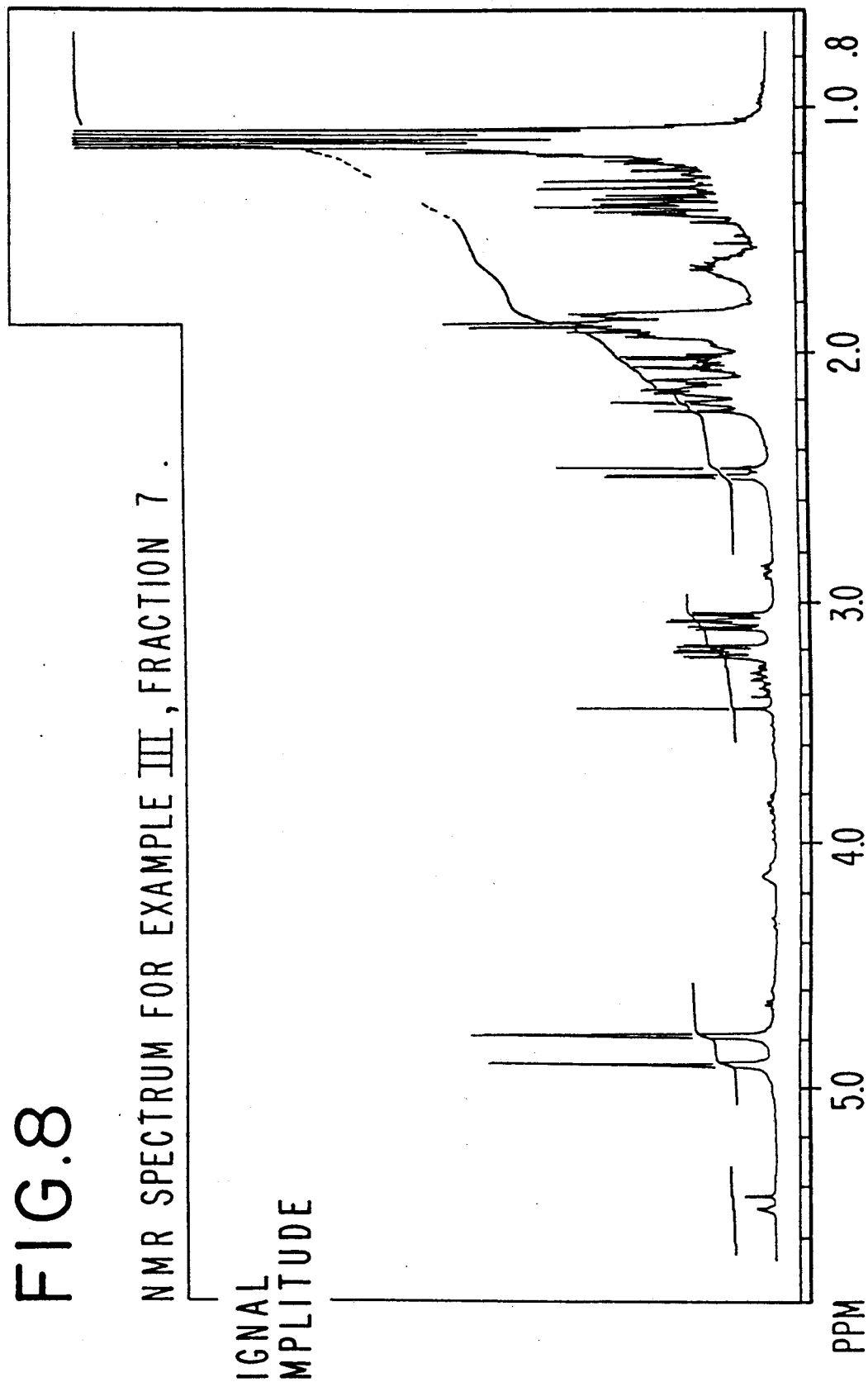

FIG. 8 is the NMR spectrum for fraction 7 of the distillation of the reaction product of Example III; for the compound having the structure:

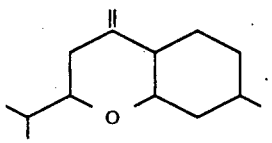

Figure 9:
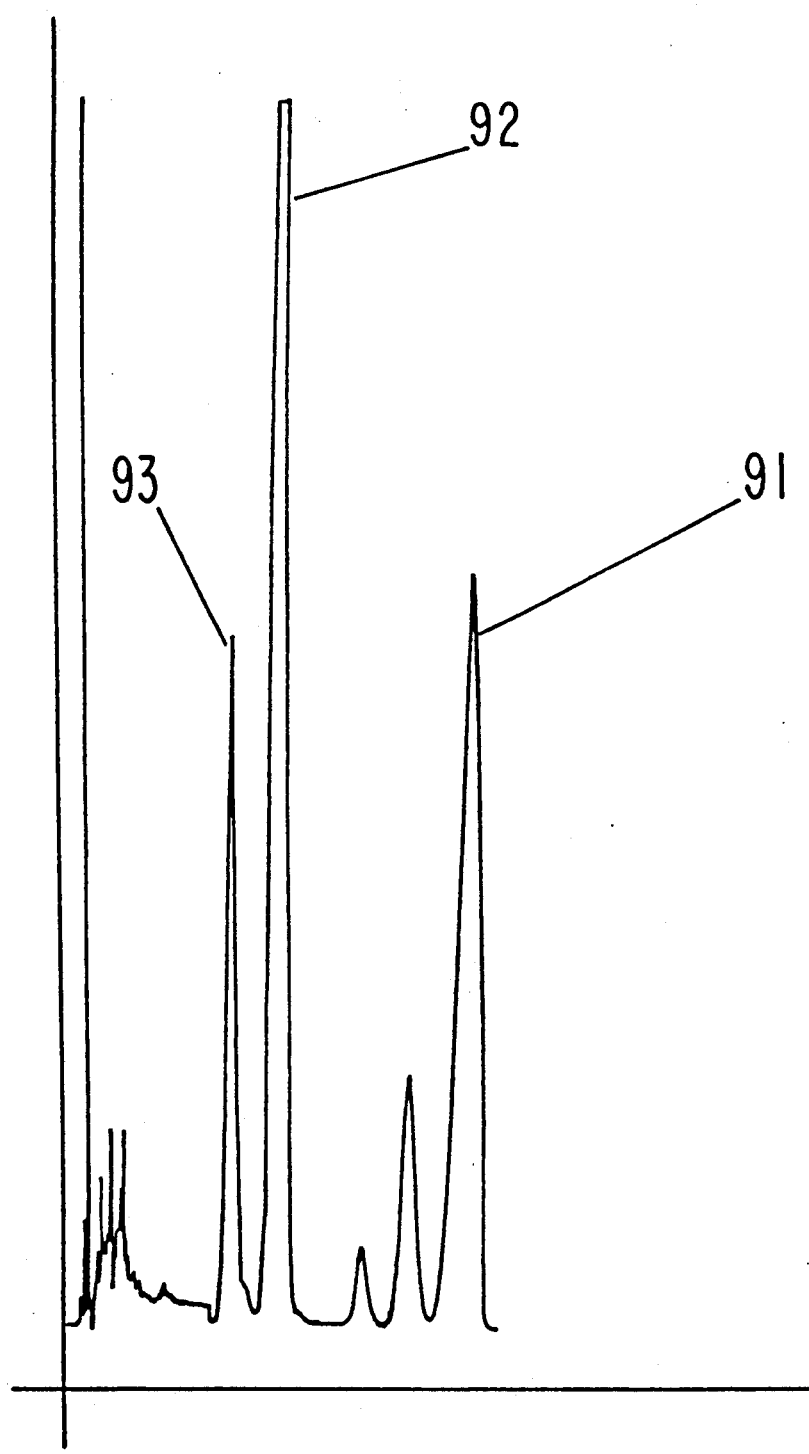

FIG. 9 is the GLC profile for the reaction product of Example IV containing the compounds having the structures:

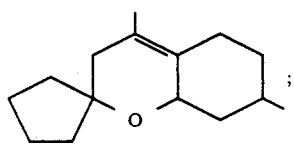

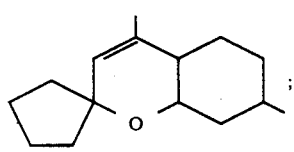

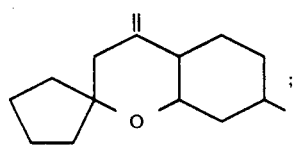

and

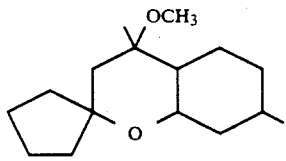

(Conditions: SE-30 column programmed at 200° C. isothermal).

Figure 10:
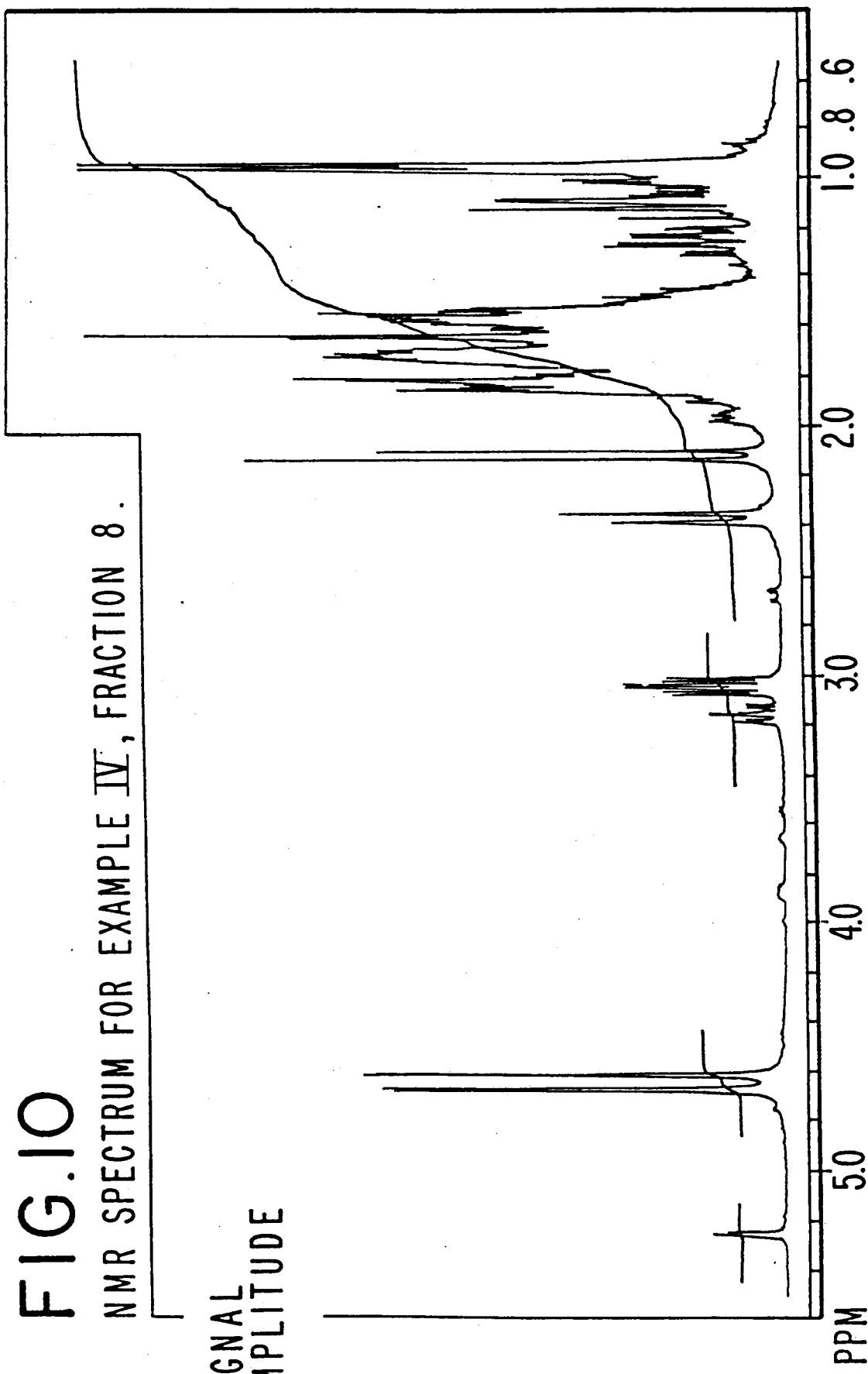

FIG. 10 is the NMR spectrum for fraction 8 of the distillation of the reaction product of Example IV for the compound having the structure:

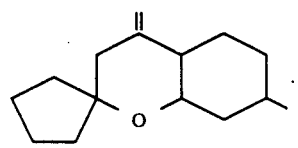

Figure 11:
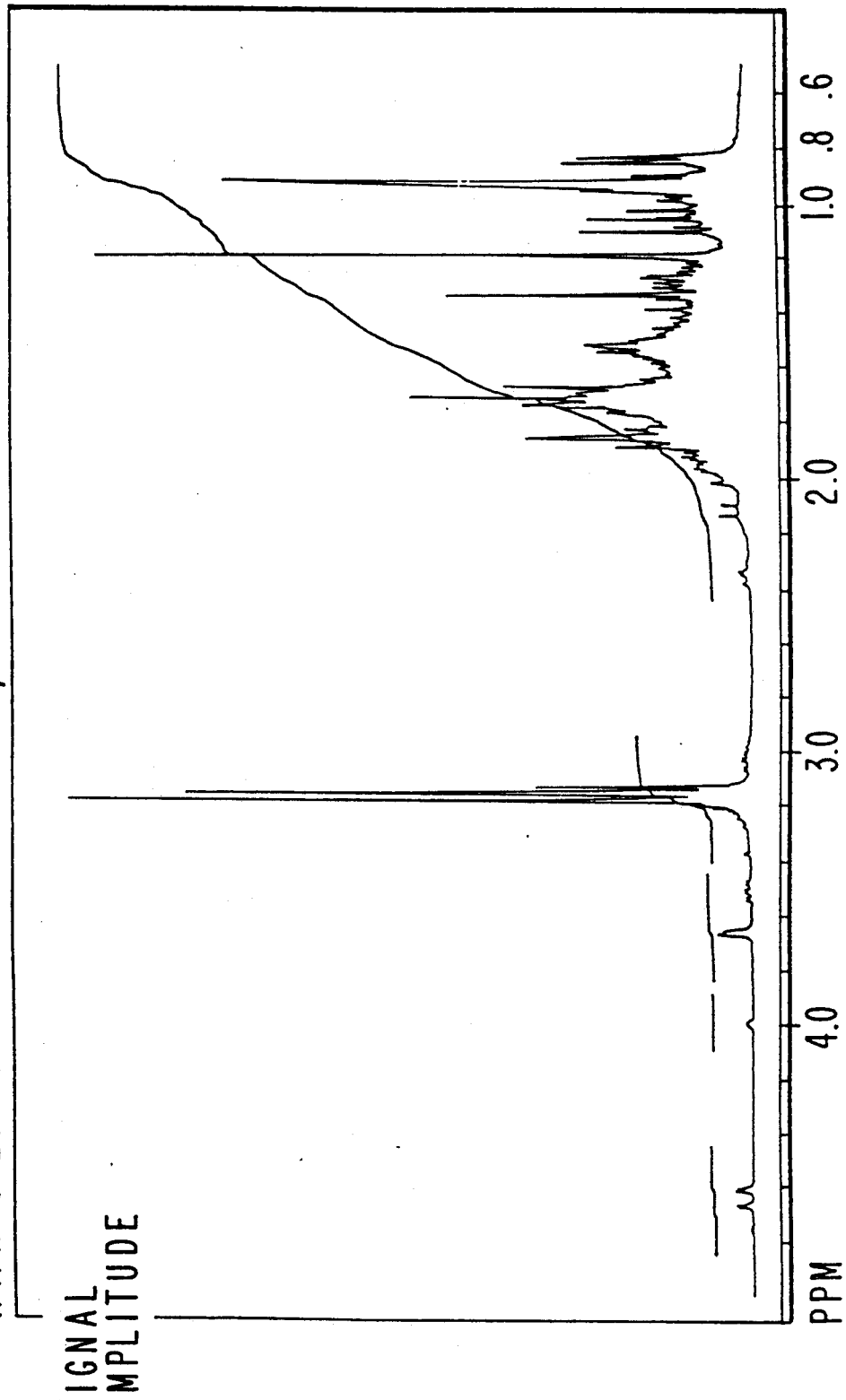

FIG. 11 is the NMR spectrum for fraction 12 of the distillation of the reaction product of Example IV for the compound having the structure:

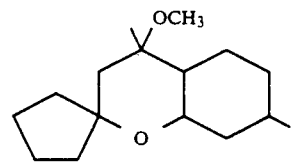

Figure 12:
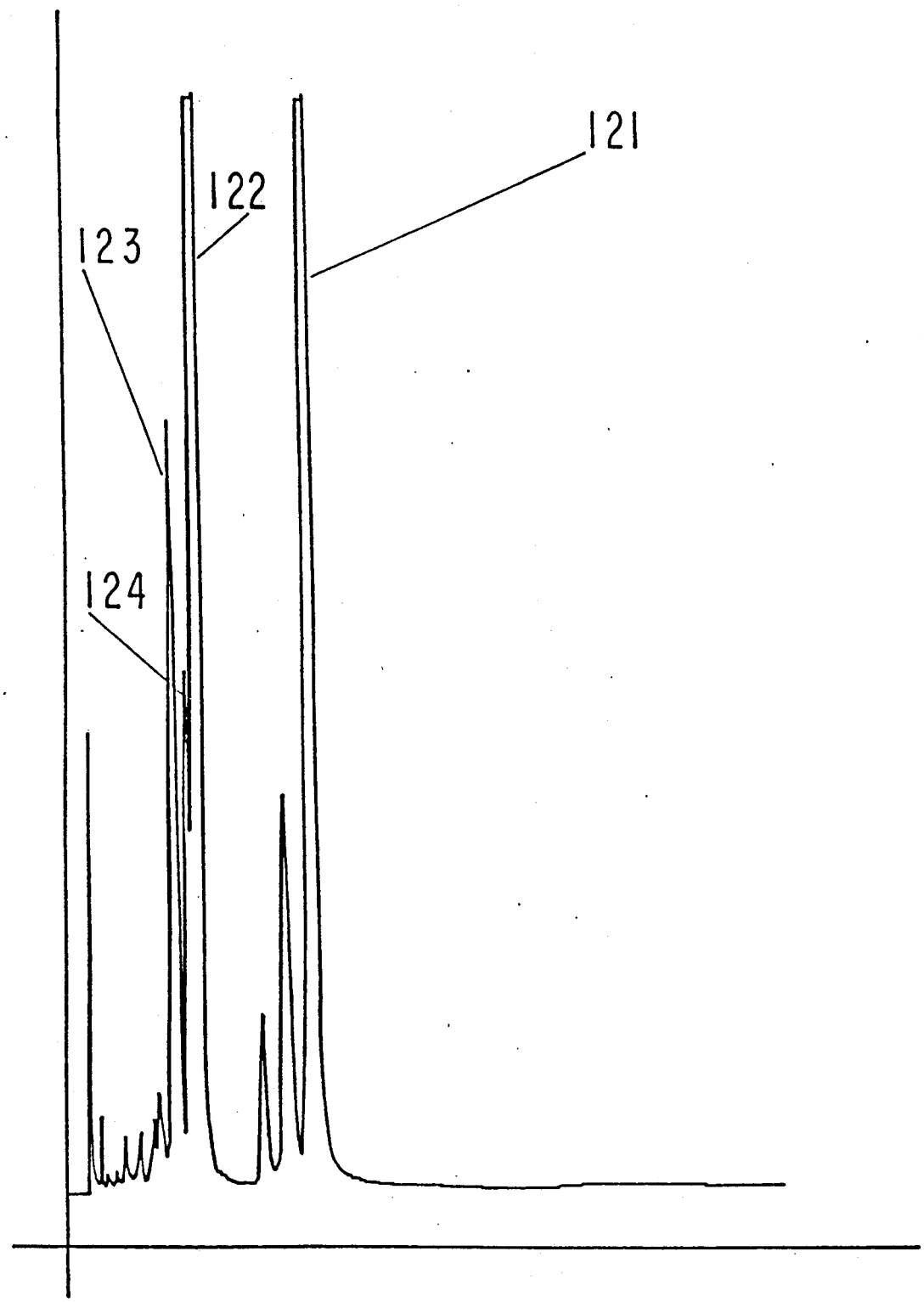

FIG. 12 is the GLC profile for the reaction product of Example V containing the compounds having the structures:

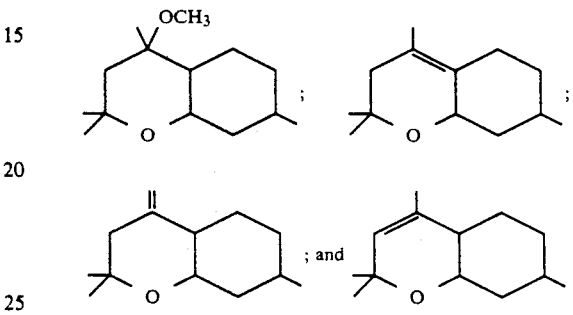

(Conditions: SE-30 column programmed at 200° C. isothermal).

Figure 13:
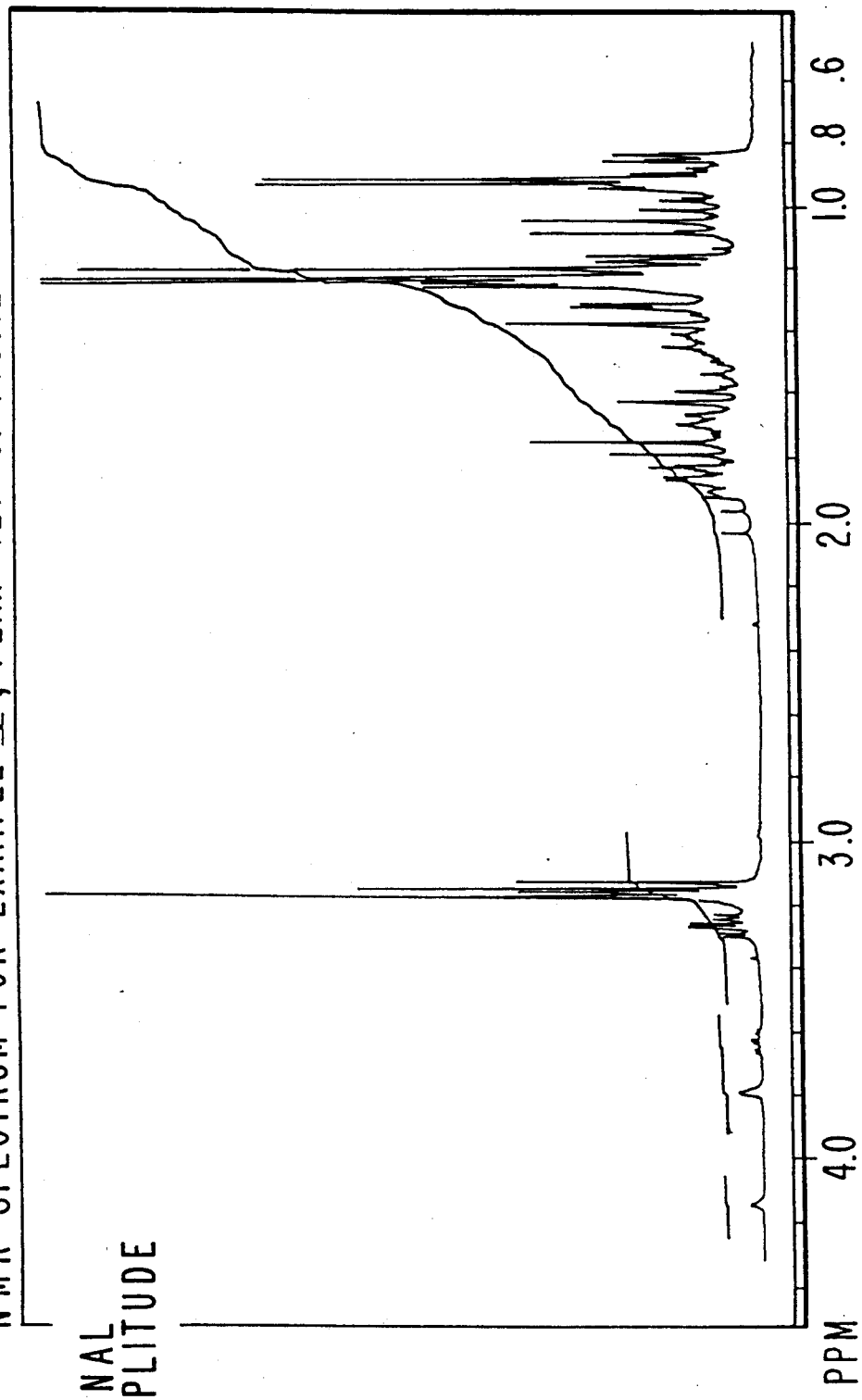

FIG. 13 is the NMR spectrum for the peak indicated by reference numeral 121 for the GLC profile of FIG. 12 for the compound having the structure:

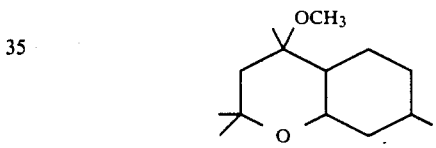

Figure 14:
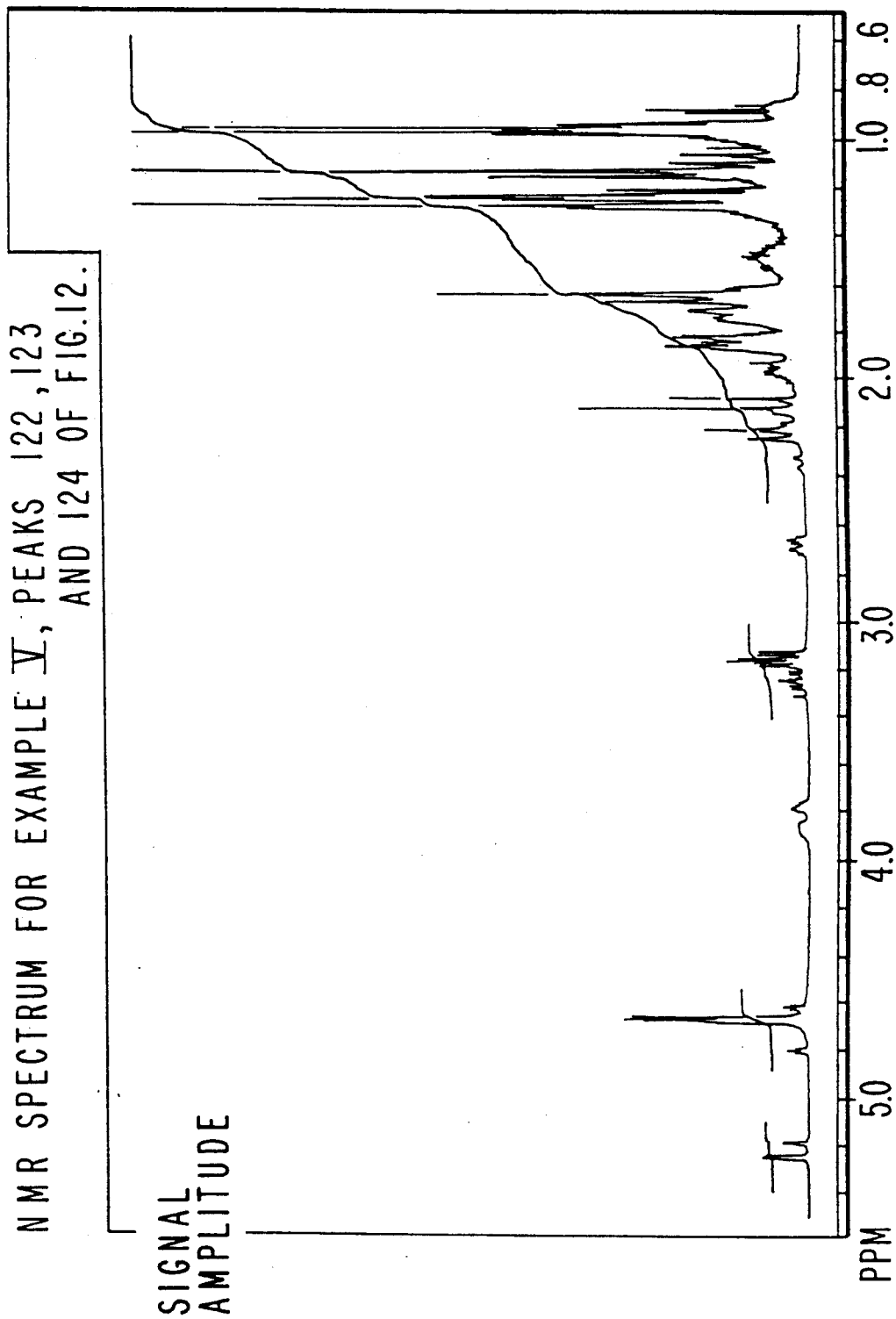

FIG. 14 is the NMR spectrum for the peaks indicated by reference numerals 122, 123 and 124 of the GLC profile of FIG. 12 for the mixture of compounds defined according to the structure:

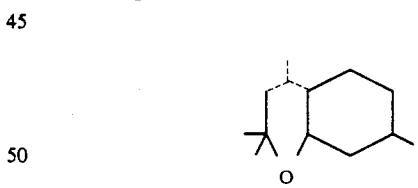

wherein in the mixture in each of the compounds one of the dashed lines is a carbon-carbon double bond and each of the other of the dashed lines are carbon-carbon single bonds.

Figure 15:
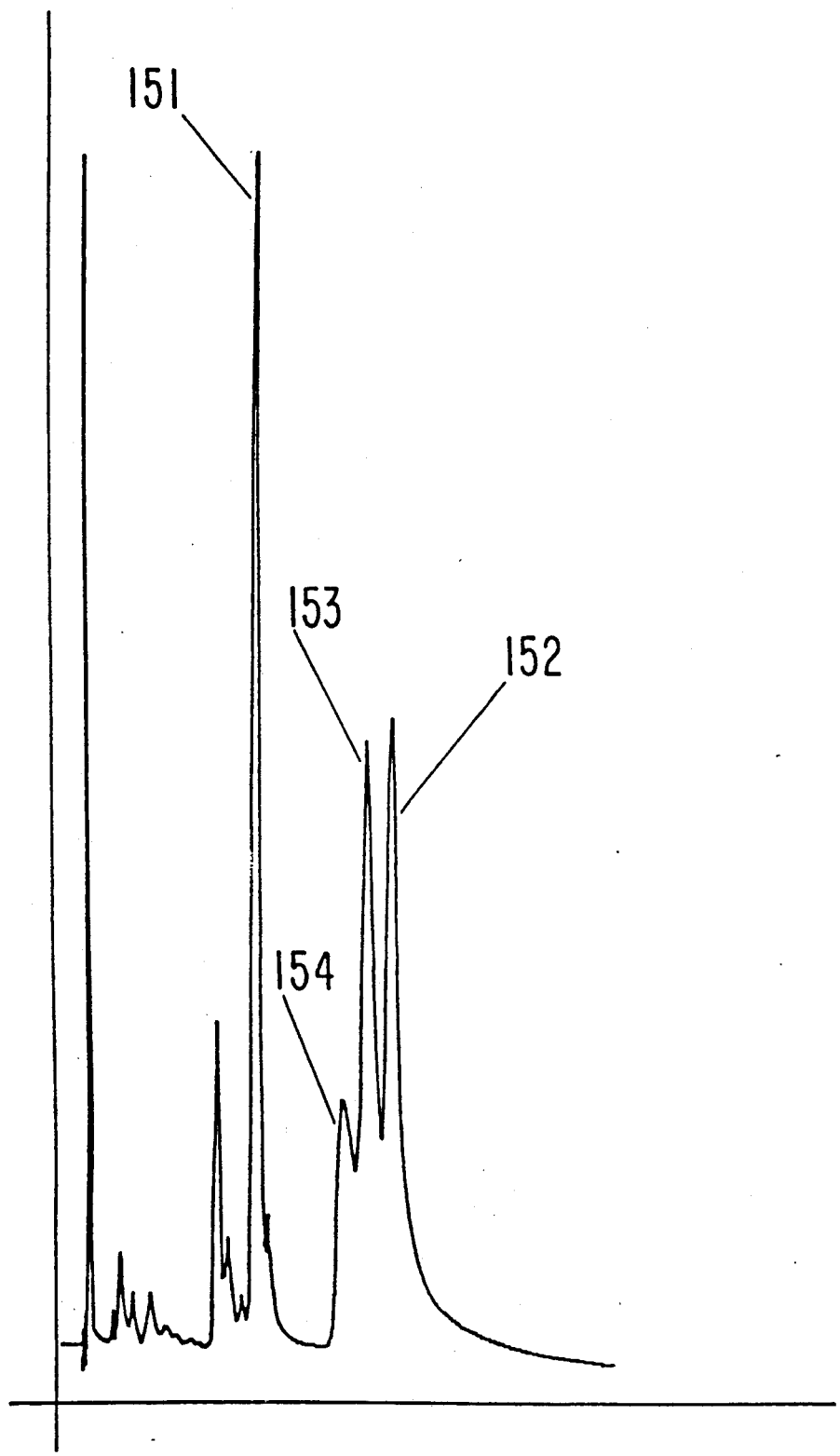

FIG. 15 is the GLC profile for the reaction product of Example VI containing the compounds having the structures:

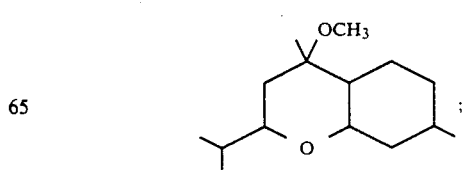

-continued

[structure diagram]

[structure diagram]

and

[structure diagram]

(Conditions: SE-30 column programmed at 200° C. isothermal).

Figure 16:
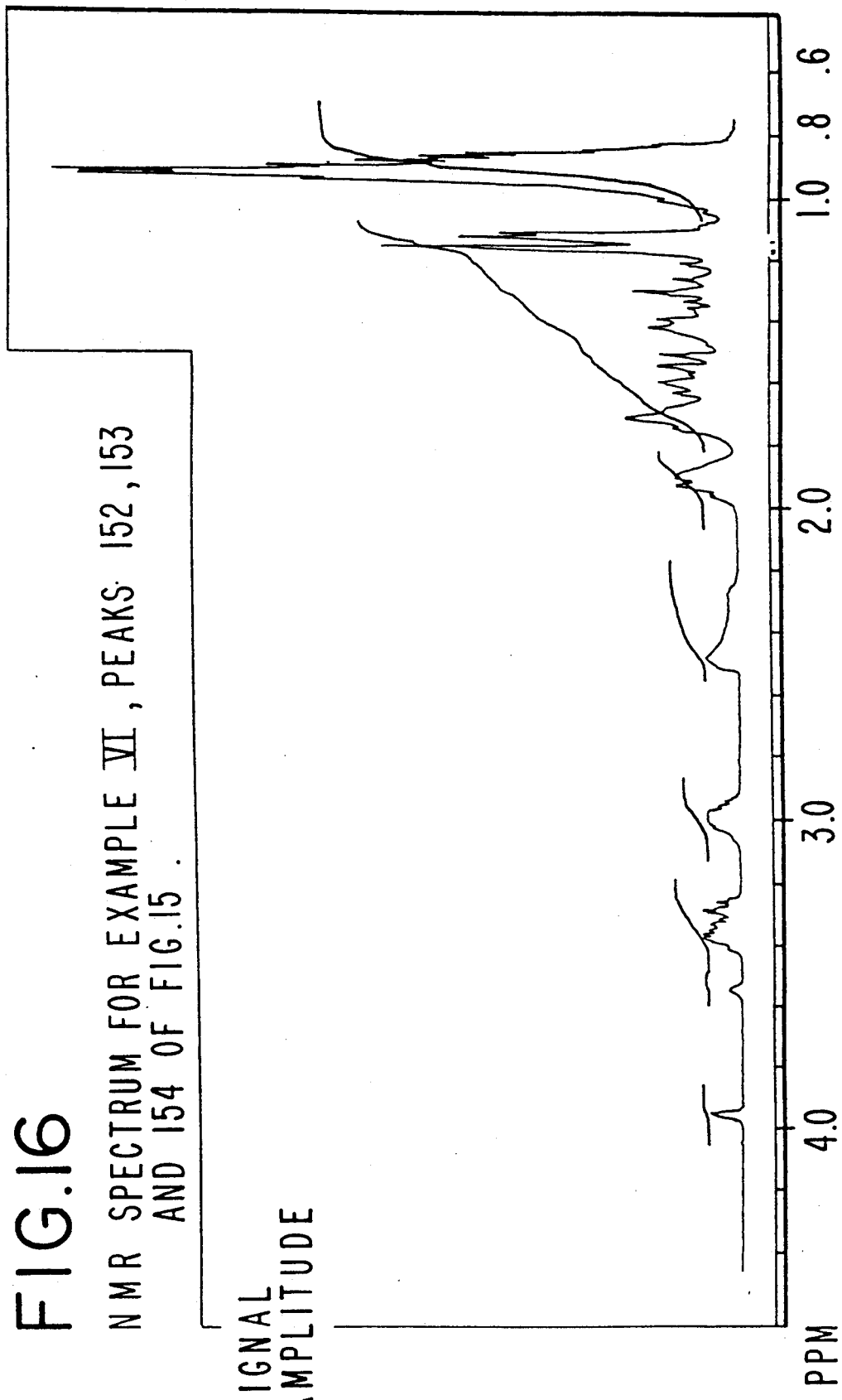

FIG. 16 is the NMR spectrum for the peaks indicated by reference numerals 152, 153 and 154 of the GLC profile of FIG. 15; for isomers of the compound having the structure:

[structure diagram with OH]

FIG. 17 is the NMR spectrum for the peak indicated by reference numeral 151 of the GLC profile of FIG. 15 for the compound having the structure:

[structure diagram]

FIG. 18 represents a cut-away side elevation view of apparatus used in forming perfumed polymers containing at least one of the alkyl-substituted tetra- or hexahydrobenzopyran derivatives of our invention.

FIG. 19 is a front view of the apparatus of FIG. 18 looking in the direction of the arrows.

DETAILED DESCRIPTION OF THE DRAWINGS

FIG. 3 is the GLC profile for the reaction product of Example II containing the compounds having the structures:

[structure diagram with OCH$_3$]

-continued

[structure diagram]

[structure diagram]

and

[structure diagram]

The peak indicated by reference numeral 31 is the peak for the compound having the structure:

[structure diagram with OCH$_3$]

The peak indicated by reference numeral 32 is the peak for the mixture of compounds having the structures:

[structure diagram]

[structure diagram]

and

[structure diagram]

FIG. 9 is the GLC profile for the reaction product of Example IV containing the compounds having the structures:

[structure diagram with OCH$_3$ and cyclopentane]

-continued

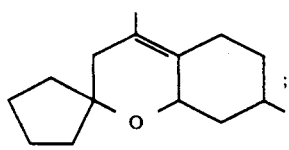

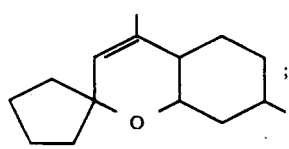

and

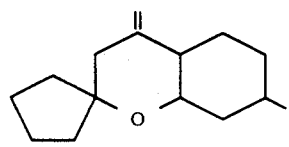

(Conditions: SE-30 column programmed at 200° C. isothermal). The peaks indicated by reference numerals 92 and 93 are the peaks for the compounds having the structures:

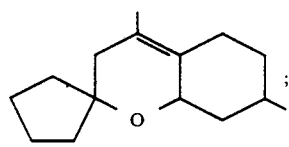

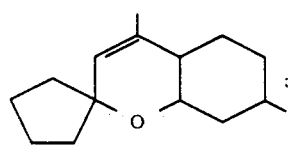

and

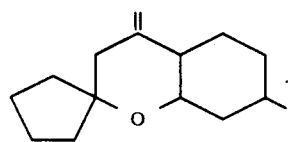

The peak indicated by reference numeral 91 is the peak for the compound having the structure:

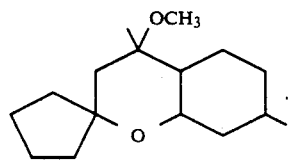

FIG. 12 is the GLC profile for the reaction product of Example V containing the compounds having the structures:

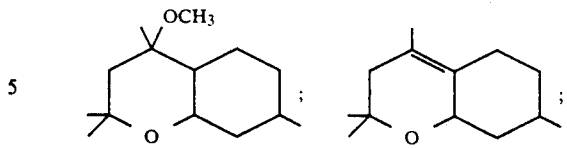

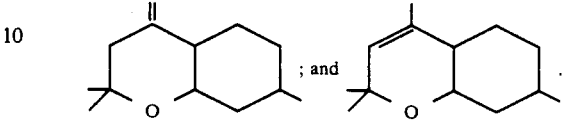

(Conditions: SE-30 column programmed at 200° C. isothermal). The peak indicated by reference numeral 121 is the peak for the compound having the structure:

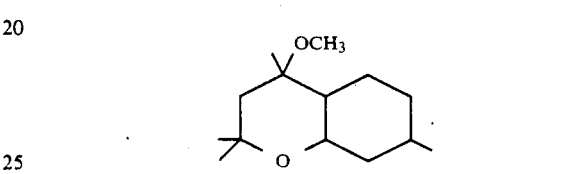

The peaks indicated by reference numerals 122, 123 and 124 are for the compounds having the structures:

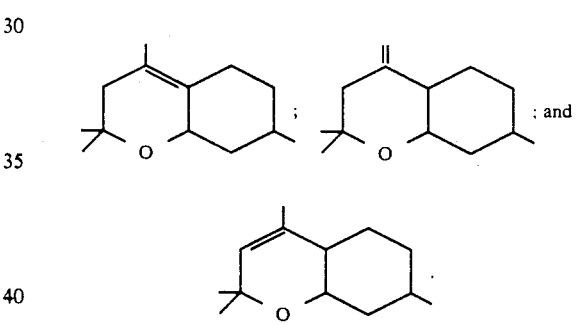

FIG. 15 is the GLC profile for the reaction product of Example VI containing the compounds having the structures:

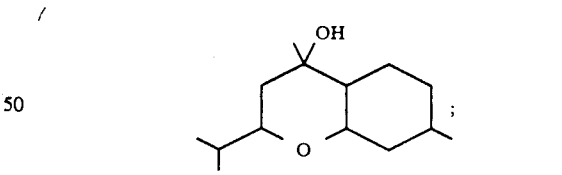

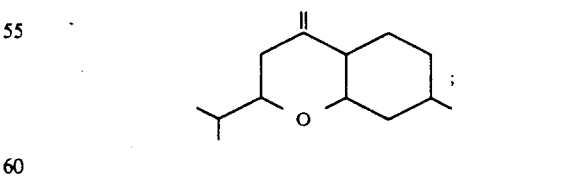

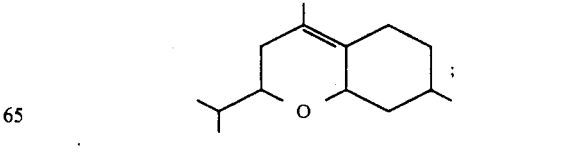

and

-continued

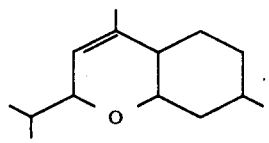

The peaks indicated by reference numerals 152, 153 and 154 are the peaks for the compound having the structure:

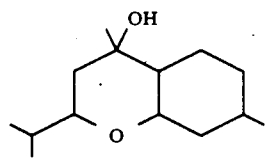

and isomers thereof. The peak indicated by reference numeral 151 is the peak for the compound having the structure:

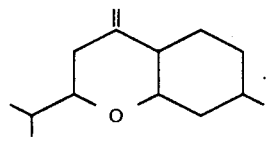

Referring to FIGS. 18 and 19, there is provided a process for forming scented polymer pellets (wherein the polymer may be a thermoplastic polymer such as low density polyethylene or polypropylene or copolymers of ethylene-vinyl acetate or mixtures of a polymer and copolymer such as a copolymer of ethylene-vinyl acetate and polyethylene) such as pellets useful in the formation of plastic particles useful in fabricating certain articles which may be perfumed. This process comprises heating the polymer or mixture of polymers to the melting point of said polymer or mixture of polymers, e.g., 250° C. in the case of low density polyethylene. The lower-most portion of the container is maintained at a slightly lower temperature and the material of the container is taken off at such location for delivery through the conduit. Thus, referring to FIGS. 18 and 19, in particular, the apparatus used in producing such elements comprises a device for forming the polymer containing perfume, e.g., polyethylene or polyethylene-polyvinyl acetate or mixtures of same or polypropylene, or the like, which comprises a vat or container 212 into which the polymer taken alone or in admixture with other copolymers and a perfuming substance containing at least one of the alkyl-substituted tetra-or hexahydrobenzopyran derivatives of our invention is placed. The container is closed by means of an air-tight lid 228 and clamped to the container by bolts 265. A stirrer 273 traverses the lid or cover 228 in an air-tight manner and is rotatable in a suitable manner.

A surrounding cylinder 212A having heated coils which are supplied with electric current through cable 214 from a rheostat or control 216 is operated to maintain the temperature inside the container 212 such that the polymer in the container will be maintained in the molten or liquid state. It has been found advantageous to employ polymers at such a temperature that the viscosity will be in the range of 90–100 sayboldt seconds.

Heating means (coils 212A) are operated to maintain the upper portion of the container 212 within a temperature range of, for example, 250°-260° C. in the case of low density polyethylene. The bottom portion of the container 212 is also heated by means of heating coils 212A regulated through the control 220 connected thereto through a connecting wire 222 to maintain the lower portion of the container 212 with a temperature range of 225°-240° C.

Thus, the polymer or mixture of polymers added to the container 212 is heated from 10-12 hours, whereafter the perfume composition or perfume material containing at least one of the alkyl-substituted tetra- or hexahydrobenzopyran derivatives of our invention is quickly added to the melt. Generally, about 10-45 percent by weight of the resulting mixture of the perfumery substance is added to the polymer.

After the perfume material containing at least one of the alkyl-substituted tetra- or hexahydrobenzopyran derivatives of our invention is added to the container 212, the mixture is stirred for a few minutes, for example, 5-15 minutes and maintained within the temperature ranges indicated previously by the heating coils 212A. The controls 216 and 220 are connected through cables 224 and 226 to a suitable supply of electric current for supplying the power for heating purposes.

Thereafter, the valve "V" is opened permitting the mass to flow outwardly through conduit 232 (also indicated by reference numeral 218 in FIG. 18) having a multiplicity of orifices 234 adjacent to the lower side thereof. The outer end of the conduit 232 is closed so that the liquid polymer intimately admixed with at least one of the alkyl-substituted tetra- or hexahydrobenzopyran derivatives of our invention will continuously drop through the orifices 234 downwardly from the conduit 232. During this time, the temperature of the polymer intimately admixed with the perfumery substance in the container 212 is accurately controlled so that a temperature in the range of from about 240°-250° C. (in the case of low density polyethylene) will exist in the conduit 232. The regulation of the temperature through the controls 216 and 220 is essential in order to insure temperature balance to provide for the continuous dropping or dripping of molten polymer intimately admixed with the perfume substance containing at least one of the alkyl-substituted tetra- or hexahydrobenzopyran derivatives of our invention through the orifices 234 at a rate which will insure the formation of droplets 236 which will fall downwardly onto a moving conveyor belt 238 caused to run between conveyor wheels 240 and 242 beneath the conduit 232.

When the droplets 236 fall onto the conveyor 238, they form pellets 244 which harden almost instantaneously and fall off the end of the conveyor 238 into a container 250 which is advantageously filled with water or some other suitable cooling liquid to insure the rapid cooling of each of the pellets 244. The pellets 244 are then collected from the container 250 and utilized for formation of other functional products, e.g., garbage bags and the like.

SUMMARY OF THE INVENTION

Our invention relates to alkyl-substituted tetra- or hexahydrobenzopyran derivatives defined according to the structure:

13

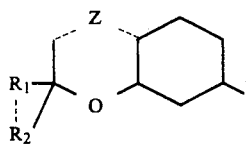

as well as the structure:

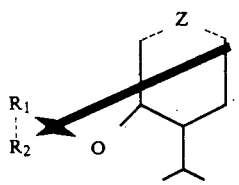

wherein Z is a moiety selected from the group consisting of:

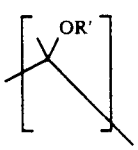

and

and wherein R' is methyl or ethyl; wherein in the moiety:

one of the dashed lines is a carbon-carbon double bond and the other of the dashed lines are carbon-carbon single bonds; and wherein $R_1$ and $R_2$ taken separately are hydrogen or $C_1$-$C_3$ lower alkyl or $R_1$ and $R_2$ taken together complete a $C_5$ or $C_6$ cycloalkyl moiety.

Our invention also relates to organoleptic uses of such alkyl-substituted tetra- or hexahydrobenzopyran derivatives as defined, supra, in augmenting or enhancing the aroma of perfume compositions, colognes or perfumed articles, including but not limited to solid or liquid anionic, cationic, nonionic or zwitterionic detergents, fabric softener compositions, fabric softener articles, hair preparations, cosmetic powders and perfumed polymers.

Our invention is also related to processes for preparing such alkyl-substituted tetra- or hexahydrobenzopyran derivatives by means of reacting isopulegol having the structure:

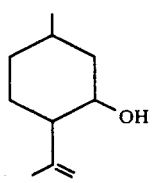

14 or an isomer thereof having the structure:

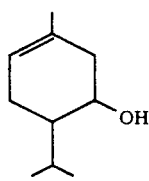

with a pre-prepared ketal or acetal having the structure:

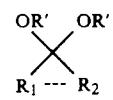

according to the reaction:

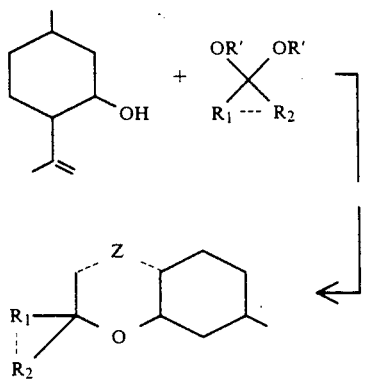

or the reaction:

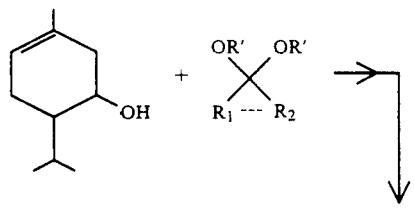

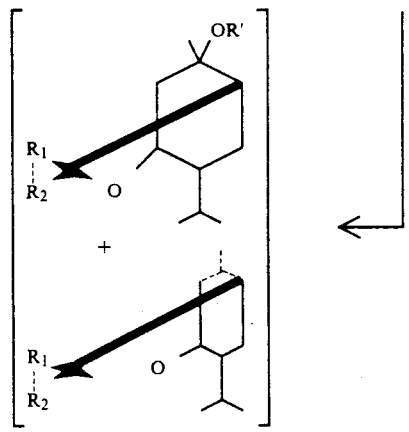

(wherein R', $R_1$, $R_2$ and Z are defined, supra).

The ketals or acetals are prepared by reacting the appropriate aldehyde or ketone with an acetal or ketal-forming reagent (e.g., a trialkylorthoformate) according to the reaction:

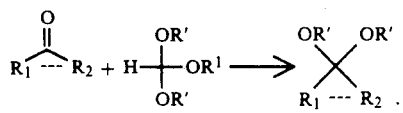

In the alternative, isopulegol per se may be reacted with an aldehyde (without the acetal formation) according to the reaction:

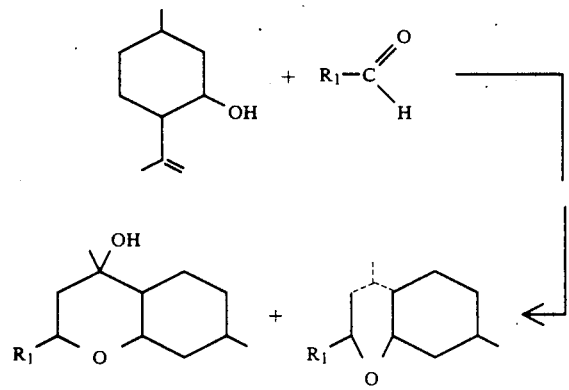

When isopulegol is used as a reagent; and when an acetal is used as a reactant, the mechanism of the reaction is as follows:

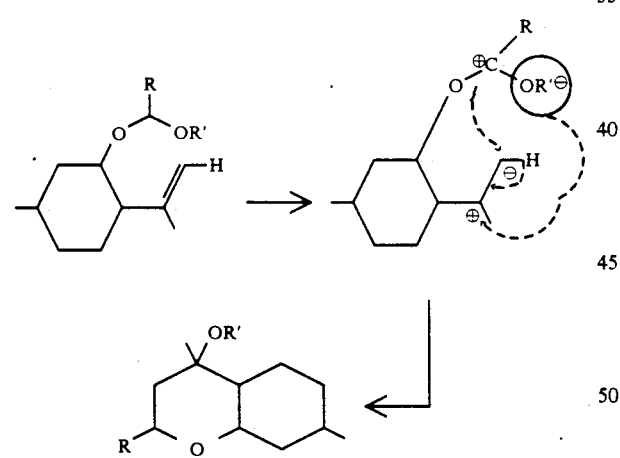

In general, when a ketal is used as a reagent, or an acetal is used as a reagent in the reaction with isopulegol the mechanism is shown as follows:

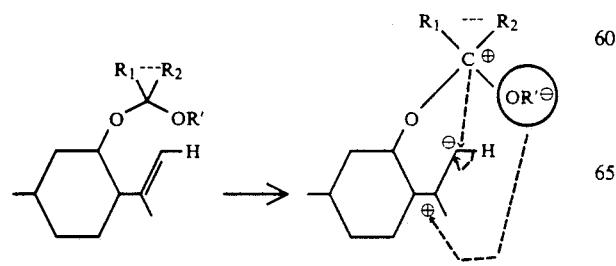

-continued

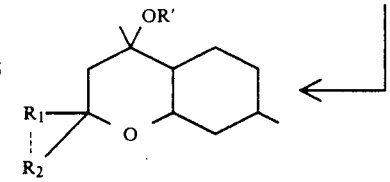

When the reaction is one which takes place between isopulegol and an aldehyde, the mechanism is as follows:

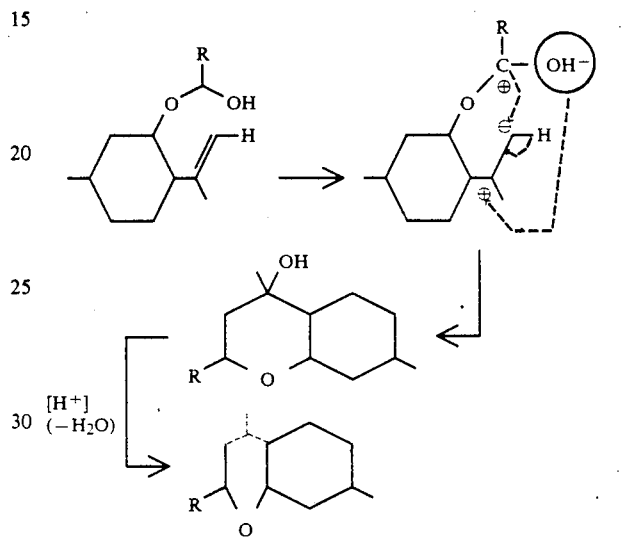

When the reaction takes place between an acetal and the isomer of isopulegol having the structure:

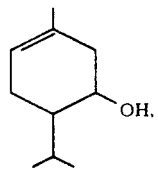

the mechanism is as follows:

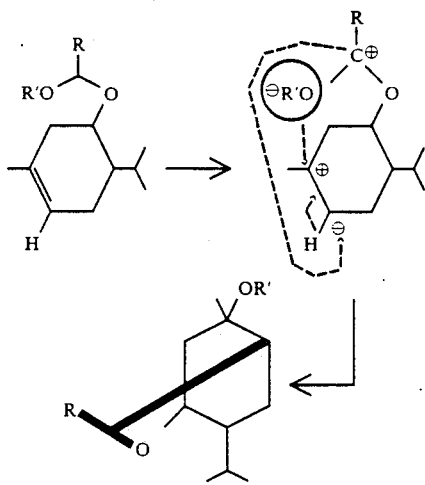

When the reaction takes place between a ketal or acetal and the isomer of isopulegol having the structure:

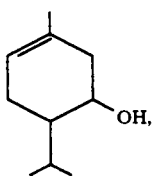

the mechanism is as follows:

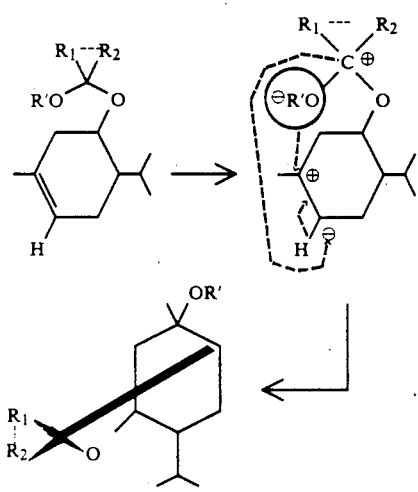

The reaction temperature (between the isopulegol or isopulegol isomer and the acetal, ketal or aldehyde (as the case may be)) may vary between about 75° C. and 100° C. depending upon the particular acetal used.

The reaction takes place in the presence of a catalytic amount of protonic acid, preferably concentrated sulfuric acid (as more specifically set forth in the examples). The reaction takes place over a period time of between about one hour and about three hours.

The mole ratio of aldehyde or ketone to isopulegol or isopulegol isomer may vary from about 2 moles (aldehyde or ketone):1 mole isopulegol or isopulegol isomer down to about 1 mole (aldehyde or ketone):1 mole isopulegol or isopulegol isomer.

At the end of the reaction the reaction mass is neutralized and the organic phase is preferably dried and fractionally distilled in order to yield organoleptically suitable product useful for incorporation into perfume compositions, colognes and/or perfumed articles.

The following Table I sets forth examples of compounds produced according to the foregoing processes and their organoleptic properties:

TABLE I

| Structure of Compound(s) And Source: | Organoleptic Properties |
|---|---|
| Mixture of compounds having the structures: | A floral, magnolia, fruity, and peach aroma with herbaceous, peach and celery-like undertones. |

TABLE I-continued

| Structure of Compound(s) And Source: | Organoleptic Properties |
|---|---|
| and produced according to Example I, distillation fraction 12. | |
| The compound having the structure: produced according to Example II, distillation fraction 10. | A peach and coconut aroma profile. |
| Mixture of compounds having the structures: and prepared according to Example II, distillation fraction 1. | A sweet, coumarin-like aroma profile with jasmine topnotes. |
| Mixture of compounds having the structures: and | A natural liatrix-like, hay-like aroma profile. |

TABLE I-continued

| Structure of Compound(s) And Source: | Organoleptic Properties |
|---|---|
| 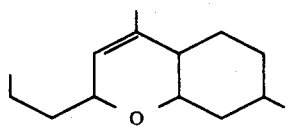<br>prepared according to Example II, distillation fraction 7. | |
| Mixture of compounds having the structures:<br>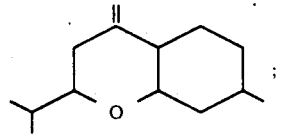<br>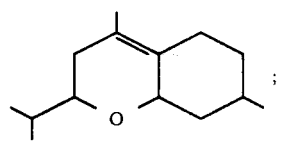<br>and<br>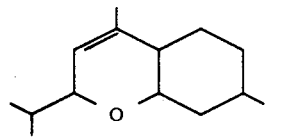<br>prepared according to Example III, distillation fraction 7. | A jasmine and lactonic aroma profile with jasmine and lactonic undertones. |
| Mixture of compounds having the structures:<br>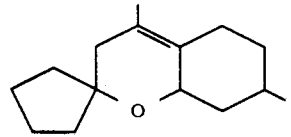<br>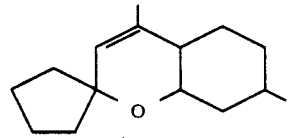<br>and<br>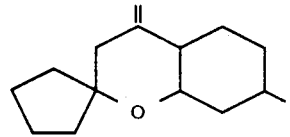<br>prepared according to Example IV, distillation fraction 8. | A woody and fruity aroma profile with citrusy, minty and buttery topnotes. |
| The compound having the structure: | A sweet and coconut aroma profile with orange peel-like |

TABLE I-continued

| Structure of Compound(s) And Source: | Organoleptic Properties |
|---|---|
| 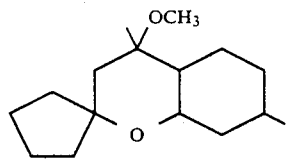<br>prepared according to Example IV, distillation fraction 12. | topnotes. |
| Mixture of compounds having the structures:<br>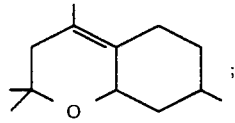<br>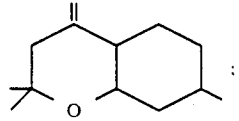<br>and<br>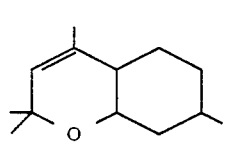<br>prepared according to Example V, bulked distillation fractions 2–7. | A minty, dry and woody aroma profile. |
| The compound having the structure:<br>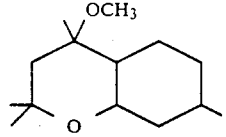<br>prepared according to Example V, bulked distillation fractions 11–16. | A woody and coconut-like aroma profile. |
| The compound having the structure:<br>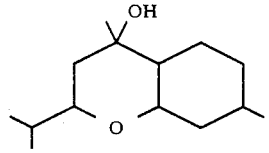<br>prepared according to Example VI, bulked distillation fractions 9–13. | A coconut-like aroma with herbaceous topnotes. |
| Mixture of compounds having the structures:<br>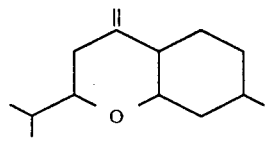 | A buttery, fruity, citrusy and green aroma profile with green, coriander seed-like and fruity undertones. |

TABLE I-continued

| Structure of Compound(s) And Source: | Organoleptic Properties |
|---|---|
| 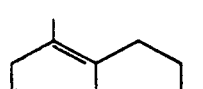 and 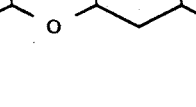 prepared according to Example VI, bulked distillation fractions 4–6. | |

At least one of the alkyl-substituted tetra- or hexahydrobenzopyran derivatives of our invention and one or more auxiliary perfume ingredients including, for example, alcohols other than the alkyl-substituted tetra- or hexahydrobenzopyran derivatives of our invention, aldehydes, nitriles, esters, cyclicesters, ketones, ethers other than the alkyl-substituted tetra- or hexahydrobenzopyran derivatives of our invention, natural essential oils and synthetic essential oils may be admixed so that the combined odors of the individual components produce a pleasant and desired fragrance particularly and preferably in floral and "tropical" fragrances.

Such perfume compositions usually contain (a) the main note or "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low-boiling, fresh smelling materials.

In perfume compositions, it is the individual components which contribute to its particular olfactory characteristics, but the over-all effect of the perfume composition will be the sum of the effects of each of the ingredients. Thus, one or more of the alkyl-substituted tetra- or hexahydrobenzopyran derivatives of our invention and one or more auxiliary perfume ingredients can be used to alter the aroma characteristics of a perfume composition, for example, by utilizing or moderating the olfactory reaction contributed by at least one other ingredient in the composition.

The amount of at least one of the alkyl-substituted tetra-or hexahydrobenzopyran derivatives of our invention useful in perfume compositions for augmentation or enhancement of floral, magnolia, fruity, citrusy, peach, natural liatrix-like, green, hay-like, lactonic, sweet, coumarin-like, coconut-like, buttery, jasmine, minty, dry and woody aromas with green, herbaceous, coriander seed-like, fruity, peach, celery-like, jasmine and lactonic undertones and citrusy, orange-peel-like, minty, herbaceous and buttery topnotes may vary from about 1% by weight of the perfume composition up to 100% by weight of the perfume composition (the entire composition can be composed of the alkyl-substituted tetra- or hexahydrobenzopyran derivatives of our invention).

At least one of the alkyl-substituted tetra- or hexahydrobenzopyran derivatives of our invention and one or more auxiliary perfume ingredients can be used to impart such aroma nuances, topnotes and undertones to soaps, anionic, cationic, nonionic or zwitterionic detergents, fabric softener compositions, fabric softener articles, cosmetic powders, hair preparations and the like. The amount employed can range up to 100% by weight of the fragrance components and can range up to approximately 0.5% of the weight of the perfumed article and will depend upon considerations of cost, nature of the end product, the effect desired on the finished product and the particular fragrance sought.

At least one of the alkyl-substituted tetra- or hexahydrobenzopyran derivatives of our invention and one or more auxiliary perfume ingredients are useful, taken alone or in perfume compositions as olfactory components in anionic, cationic, nonionic or zwitterionic detergents, soaps, fabric softener compositions, fabric softener articles for use in clothes dryers (e.g., "BOUNCE ®", a registered trademark of the Procter & Gamble Company of Cincinnati, Ohio), space odorants and deodorants, perfumes, colognes, toilet waters, bath preparations, such as lacquers, brilliantines, creams, deodorants, hand lotions and sun screens; powders, such as talcs, dusting powders, face powders and the like.

When used as an olfactory component in perfume compositions or perfumed articles, such as anionic, cationic, nonionic or zwitterionic detergents and fabric softener compositions and fabric softener articles (e.g., for use in clothing dryers) as little as 0.05% of at least one of the alkyl-substituted tetra-or hexahydrobenzopyran derivatives of our invention and one or more auxiliary perfume ingredients will suffice to impart aroma nuances as set forth, supra. Generally, no more than 0.5% of at least one of the alkyl-substituted tetra- or hexahydrobenzopyran derivatives of our invention and one or more auxiliary perfume ingredients based on the ultimate end product is required in the perfumed article.

In addition, the perfume composition or fragrance composition of our invention can contain a vehicle or carrier for at least one of the alkyl-substituted tetra- or hexahydrobenzopyran derivatives of our invention and one or more auxiliary perfume ingredients. The vehicle can be a liquid such as a non-toxic alcohol, a non-toxic glycol, or the like. The carrier can also be an absorbent solid, such as a gum (e.g., gum arabic, xanthan gum or guar gum) or components for encapsulating the composition (such as gelatin as by means of coacervation).

It will thus be apparent that at least one of the alkyl-substituted tetra- or hexahydrobenzopyran derivatives of our invention and one or more auxiliary perfume ingredients can be used to alter the sensory properties, particularly organoleptic properties of a wide variety of consumable materials.

The following Examples I–VI are illustrative of processes for preparing the alkyl-substituted tetra- or hexahydrobenzopyran derivatives of our invention. Examples VII, et seq. are illustrative of the organoleptic utilities of the alkyl-substituted tetra- or hexahydrobenzopyran derivatives of our invention. However, the invention is to be considered restricted thereto only as indicated in the appended claims.

All parts and percentages given herein are by weight unless otherwise specified.

EXAMPLE I

Reaction of Isopulegol with Propionaldehyde

Reaction:

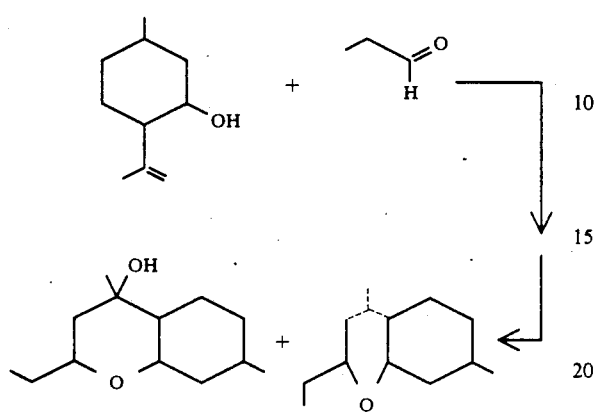

(wherein the compound indicated thusly:

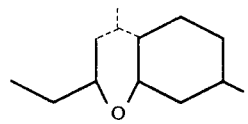

in the mixture in each of the compounds one of the dashed lines represents a carbon-carbon double bond and each of the other of the dashed lines represent carbon-carbon single bonds).

Into a 2 liter reaction vessel equipped with stirrer, thermometer, heating mantle, reflux condenser and addition funnel is placed 296 grams of propionaldehyde. The propionaldehyde is heated to reflux and during refluxing over a period of one hour, 693 grams of isopulegol is added to the reaction mass. The reaction mass is then maintained for 0.5 hours at 75° C. with stirring. The reaction mass is then cooled to 50° C. and 1 liter of water is added. The organic phase is then washed with a 10% sodium carbonate solution (one equal volume). The organic phase is then distilled yielding the following fractions:

| Fraction No. | Vapor Temp. (°C.) | Liquid Temp. (°C.) | Vacuum mm/Hg. Pressure | Reflux Ratio |
|---|---|---|---|---|
| 1 | 23/97 | 23/108 | 4.0 | 100% |
| 2 | 97 | 110 | 4.0 | 9:1 |
| 3 | 97 | 110 | 4.0 | 9:1 |
| 4 | 97 | 110 | 4.0 | 9:1 |
| 5 | 100 | 80 | 3.0 | 4:1 |
| 6 | 100 | 110 | 3.0 | 4:1 |
| 7 | 100 | 110 | 3.0 | 4:1 |
| 8 | 98 | 112 | 3.0 | 4:1 |
| 9 | 98 | 112 | 3.0 | 4:1 |
| 10 | 98 | 113 | 3.0 | 4:1 |
| 11 | 99 | 114 | 3.0 | 4:1 |
| 12 | 99 | 116 | 3.0 | 4:1 |
| 13 | 99 | 119 | 3.0 | 4:1 |
| 14 | 99 | 124 | 3.0 | 4:1 |
| 15 | 99 | 129 | 3.0 | 4:1 |
| 16 | 99 | 138 | 3.0 | 4:1 |
| 17 | 94 | 163 | 3.0 | 4:1 |
| 18 | 97 | 182 | 3.0 | 4:1 |
| 19 | 98 | 210 | 3.0 | 4:1. |

Figure 1:
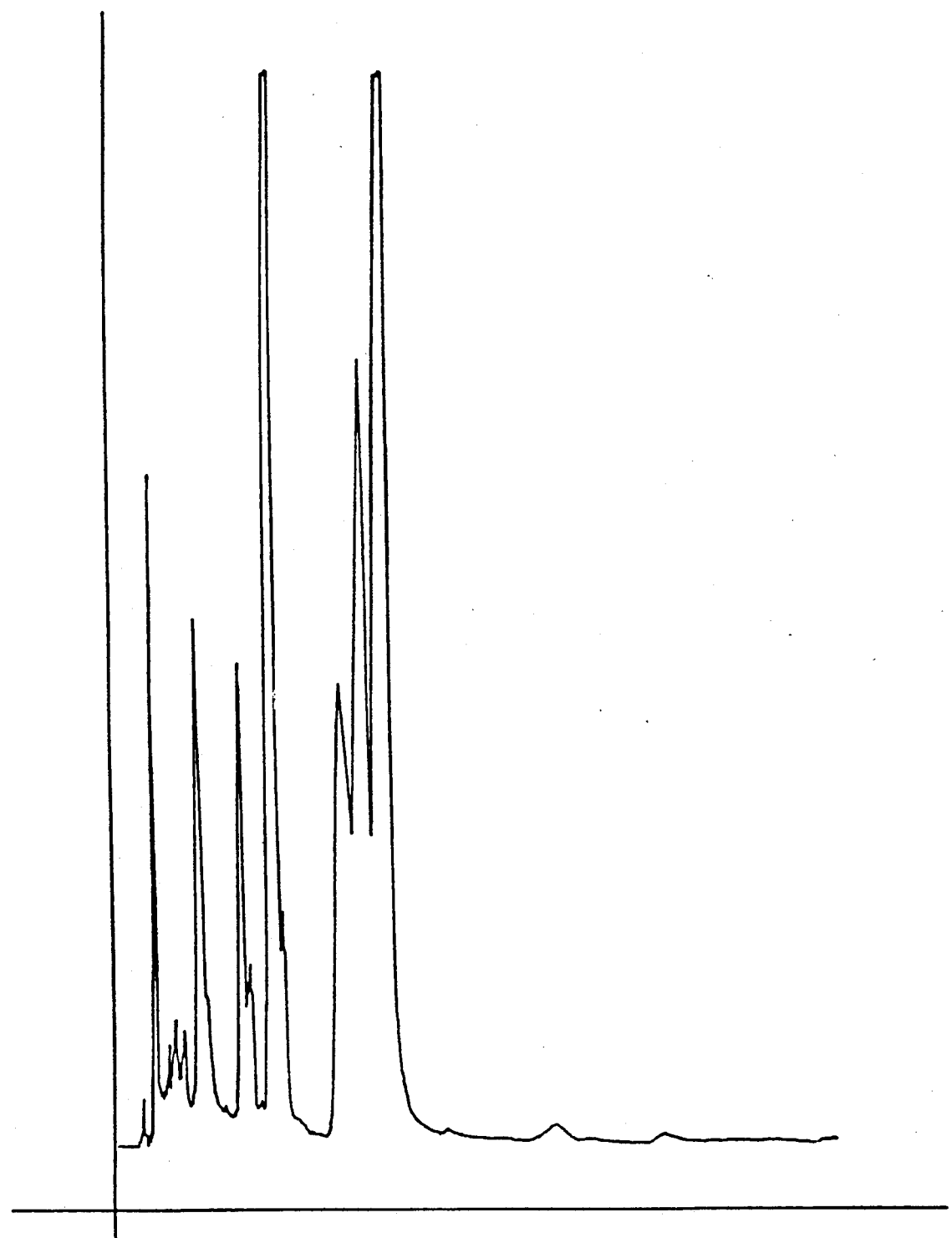
FIG. 1 is the GLC profile for the reaction product of Example I containing the compounds having the structures.

FIG. 1 is the GLC profile for the resulting reaction product.

FIG. 2 is the NMR spectrum for the mixture of compounds having the structures:

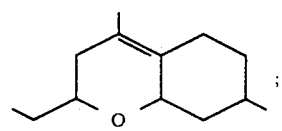

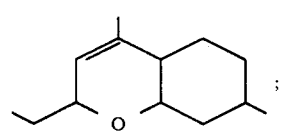

and

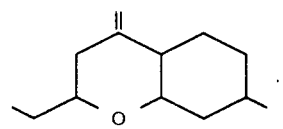

The mixture of compounds having the structures:

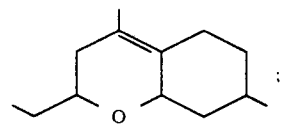

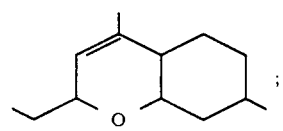

and

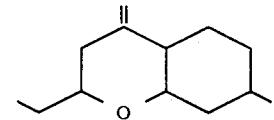

(distillation fraction 12) has a floral, magnolia, fruity, and peach aroma profile with herbaceous, peach and celery-like undertones.

EXAMPLE II

Reaction of Isopulegol with Dimethyl Acetal of Butyraldehyde

Reaction:

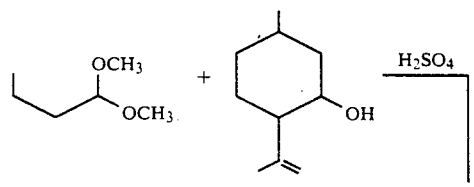

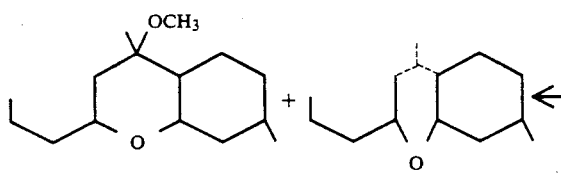

(wherein with respect to the mixture of compounds shown by the structure:

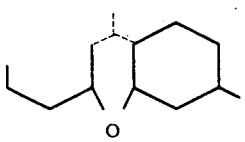

in each of the compounds one of the dashed lines is a carbon-carbon double bond and each of the other of the dashed lines represent carbon-carbon single bonds); and

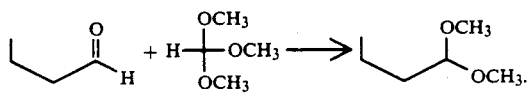

Into a 2 liter reaction vessel equipped with stirrer, thermometer, reflux condenser and addition funnel are placed 252 grams of n-butyraldehyde (3.5 moles); 424 grams of trimethyl orthoformate (4.0 moles) and 100 grams of methanol. The resulting mixture is cooled to −5° C. Over a period of 15 minutes, 3 ml concentrated hydrochloric acid is added dropwise to the reaction mass with stirring. When the addition of the hydrochloric acid is completed, the cooling apparatus is removed and the reaction mass is permitted to reach room temperature.

8.0 Grams of sodium acetate is then added to the reaction mass and the reaction mass is stirred for another 15 minutes.

Bidwell apparatus is placed on the reaction vessel and the reaction mass is then equipped with heating mantle and heated to 78° C. While maintaining the reaction mass at 78° C., over a period of 1.5 hours, a pre-prepared mixture of isopulegol (462 grams; 3 moles) and sulfuric acid (7 grams) is added dropwise to the reaction mass.

After the 1.5 hour feed addition is completed, the reaction mass is quenched by adding a mixture of 60 grams of sodium hydroxide in 200 grams of water. The reaction mass is stirred for a period of 15 minutes.

The organic phase is separated from the aqueous phase and the organic phase is then distilled on a 1.5×12" packed column yielding the following fractions:

| Fraction No. | Vapor Temp. (°C.) | Liquid Temp. (°C.) | Vacuum mm/Hg. Pressure | Reflux Ratio |
| --- | --- | --- | --- | --- |
| 1 | 65/ | 116/ | 3.6 | 3:1 |
| 2 | 95 | 123 | 3.6 | 3:1 |
| 3 | 96 | 125 | 1.0 | 3:1 |
| 4 | 98 | 127 | 4.0 | 3:1 |
| 5 | 102 | 128 | 4.0 | 3:1 |
| 6 | 105 | 131 | 4.0 | 3:1 |
| 7 | 209 | 137 | 5.0 | 3:1 |
| 8 | 116 | 142 | 6.0 | 3:1 |
| 9 | 128 | 147 | 6.0 | 3:1 |
| 10 | 130 | 150 | 7.0 | 3:1 |
| 11 | 132 | 158 | 7.0 | 3:1 |
| 12 | 132 | 175 | 7.0 | 3:1 |
| 13 | 80 | 193 | 7.0 | 3:1. |

GLC, NMR and IR analyses yield the information that the hydrocarbon mixture is included in fractions 2-8 and the methyl ether mixture is included in fractions 9-13.

Distillation fraction 10 contains the compound having the structure:

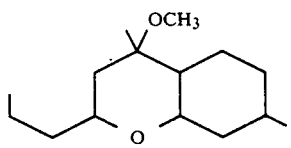

It has a peach and coconut aroma profile.

Distillation fraction 7 is a mixture of compounds having the structures:

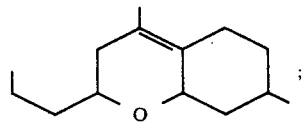

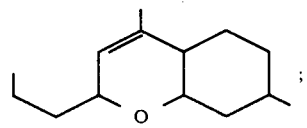

and

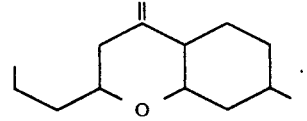

It has a natural liatrix-like and hay-like aroma profile. Distillation fraction 1 also contains the compounds having the structures:

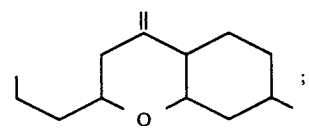

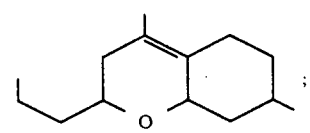

and

-continued

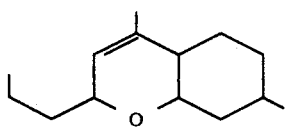

It has a sweet, coumarin-like aroma with jasmine topnotes.

FIG. 3 is a GLC profile of the reaction product prior to distillation. The peak indicated by reference numeral 32 is the peak for the mixture of compounds having the structures:

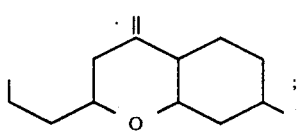

;

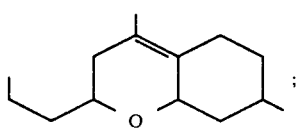

;

and

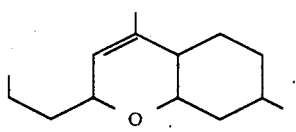

The peak indicated by reference numeral 31 is the peak for the compound having the structure:

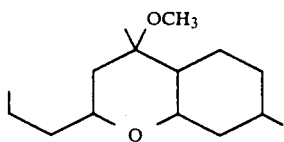

FIG. 4 is the NMR spectrum for the peak indicated by reference numeral 31 on a GLC profile of FIG. 3. This is the peak for the compound having the structure:

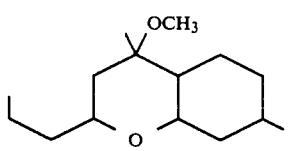

FIG. 5 is the NMR spectrum for the peak indicated by reference numeral 32 of the GLC profile of FIG. 3. This is the peak for the compound having the structure:

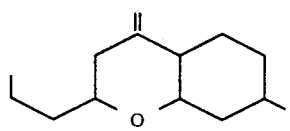

(major peak).

EXAMPLE III

Reaction of Dimethyl Acetal of Isobutyraldehyde with Isopulegol

Reactions:

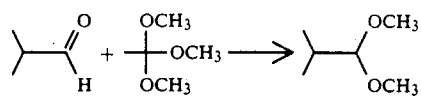

and

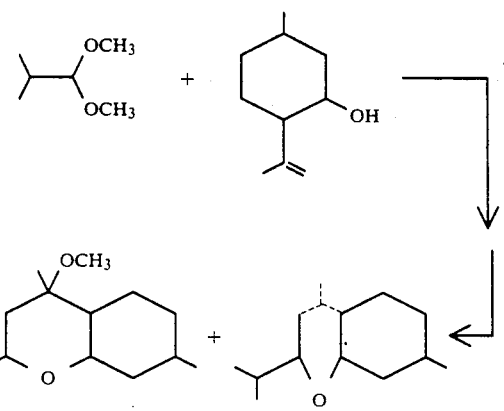

(wherein in the mixture of compounds represented by the structure:

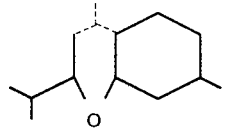

in each of the compounds one of the dashed lines represents a carbon-carbon double bond and each of the other of the dashed lines represent carbon-carbon single bonds).

Into a 2 liter reaction vessel equipped with stirrer, thermometer, reflux condenser and addition funnel and also equipped with cooling apparatus (to be replaced by heating apparatus at the appropriate time) are placed 252 grams isobutylraldehyde (3.5 moles); 424 grams of trimethyl orthoformate (4 moles) and 100 grams of methanol. The reaction mass is cooled to $-5°$ C. with stirring and over a period of 15 minutes, 3 ml concentrated hydrochloric acid is added.

When addition of the hydrochloric acid is completed, the cooling apparatus is removed and the reaction mass is allowed to reach room temperature.

8 Grams of sodium acetate is then added and the reaction mass is stirred for another 15 minutes.

A Bidwell unit is placed on the apparatus and a heating mantle is also placed on the apparatus. The reaction mass is then heated to 78° C. at which point a pre-prepared mixture of 7 grams of concentrated sulfuric acid and 462 grams (3 moles) of isopulegol is added dropwise to the reaction mass over a period of 1.5 hours (while maintaining the reaction temperature at 78° C.).

After the feed of the isopulegol-sulfuric acid reagent is completed, the reaction mass is quenched by adding prior to a mixture of 60 grams sodium hydroxide and 200 grams of water. The resulting reaction mass is stirred for 15 minutes. The organic layer is separated from the aqueous phase and the organic phase is fractionally distilled on a 1.5×15" Goodloe column yielding the following fractions:

| Fraction No. | Vapor Temp. (°C.) | Liquid Temp. (°C.) | Vacuum mm/Hg. Pressure | Reflux Ratio |
| --- | --- | --- | --- | --- |
| 1 | 63/ | 110/ | 6.0 | 3:1 |
| 2 | 68 | 110 | 6.0 | 3:1 |
| 3 | 84 | 113 | 6.0 | 3:1 |
| 4 | 90 | 116 | 6.0 | 3:1 |
| 5 | 92 | 119 | 6.0 | 3:1 |
| 6 | 93 | 124 | 6.0 | 3:1 |
| 7 | 97 | 129 | 6.0 | 3:1 |
| 8 | 102 | 135 | 6.0 | 3:1 |
| 9 | 115 | 140 | 6.0 | 3:1 |
| 10 | 109 | 139 | 5.0 | 3:1 |
| 11 | 109 | 142 | 5.0 | 3:1 |
| 12 | 110 | 146 | 5.0 | 3:1 |
| 13 | 108 | 150 | 5.0 | 3:1 |
| 14 | 112 | 165 | 5.0 | 3:1 |
| 15 | 117 | 175 | 5.0 | 3:1 |
| 16 | 120 | 183 | 5.0 | 3:1 |
| 17 | 123 | 190 | 5.0 | 3:1 |
| 18 | 153 | 210 | 3.0 | 3:1. |

Fractions 3-14 contain the compounds having the structures:

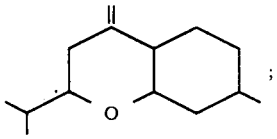

;

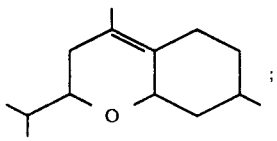

and

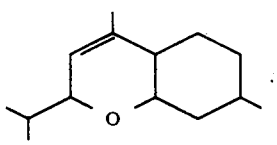

Fractions 15-18 contain the compound having the structure:

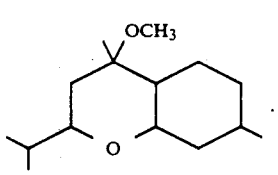

FIG. 6 is the GLC profile for the reaction product prior to distillation (Conditions: SE-30 column programmed at 180° C. isothermal).

FIG. 7 is the NMR spectrum for fraction 15 which is for the compound having the structure:

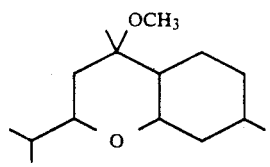

FIG. 8 is the NMR spectrum for distillation fraction 7 containing the compound having the structure:

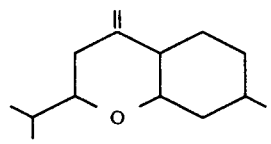

The mixture of compounds having the structures:

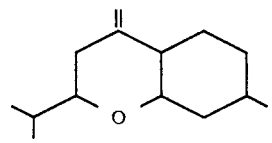

;

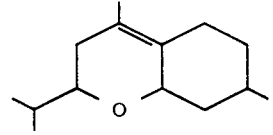

and

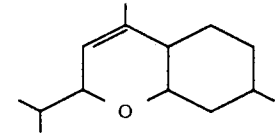

of distillation fraction 7 has a jasmine and lactonic aroma profile with jasmine and lactonic undertones.

EXAMPLE IV

Reaction of Dimethyl Ketal of Cyclopentanone with Isopulegol

Reactions:

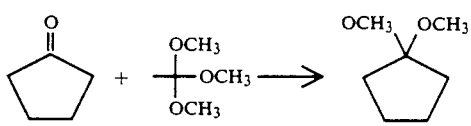

and

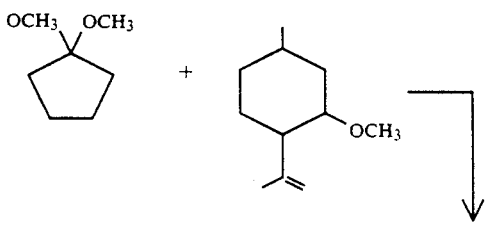

-continued

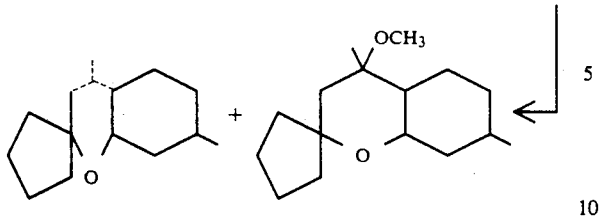

(wherein in the designation of the mixture of compounds having the structure:

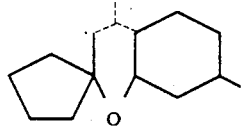

in each of the compounds one of the dashed lines represents a carbon-carbon double bond and each of the other of the dashed lines represents a carbon-carbon single bond).

Into a 2 liter reaction vessel equipped with stirrer, thermometer, reflux condenser and addition funnel and cooling apparatus is placed 294 grams (3.5 moles) of cyclopentanone, 424 grams of trimethyl orthoformate (4 moles) and 100 ml methanol. Over a period of 15 minutes, 3 ml concentrated hydrochloric acid is added to the reaction mass with stirring while maintaining the temperature of the reaction mass at $-5°$ C.

After addition of the hydrochloric acid, the cooling apparatus is removed and the reaction mass is permitted to come to room temperature. 8 Grams of sodium acetate is then added to the reaction mass with stirring and the stirring is continued for a period of 15 minutes.

The reaction apparatus is then equipped with Bidwell apparatus (for water removal) and a heating mantle.

The reaction mass, with stirring is heated to 78° C. at which point in time, a pre-prepared mixture of 7 grams of concentrated sulfuric acid and 463 grams of isopulegol (3 moles) is added dropwise over a period of 1.5 hours to the reaction mass.

After the feed is complete, the reaction mass is quenched by adding thereto a mixture of 60 grams of sodium hydroxide and 200 grams of water. The resulting reaction product is then stirred for a period of 15 minutes.

The organic phase is separated from the aqueous phase and the organic phase is distilled on a 1.5×15" Goodloe column yielding the following fractions:

| Fraction No. | Vapor Temp. (°C.) | Liquid Temp. (°C.) | Vacuum mm/Hg. Pressure | Reflux Ratio |
| --- | --- | --- | --- | --- |
| 1 | 80/ | 143/ | 4.0 | 3:1 |
| 2 | 65 | 139 | 4.0 | 3:1 |
| 3 | 110 | 140 | 4.0 | 3:1 |
| 4 | 62 | 144 | 4.0 | 1:2 |
| 5 | 118 | 153 | 4.0 | 1:1 |
| 6 | 122 | 156 | 3.0 | 1:1 |
| 7 | 122 | 158 | 3.0 | 1:1 |
| 8 | 131 | 163 | 5.0 | 1:1 |
| 9 | 133 | 168 | 5.0 | 1:1 |
| 10 | 96 | 169 | 5.0 | 1:1 |
| 11 | 116 | 165 | 5.0 | |
| 12 | 45 | 172 | 5.0. | |

FIG. 9 is the GLC profile for the reaction mass prior to distillation. The peaks indicated by reference numerals 92 and 93 are the peaks for the compounds having the structures:

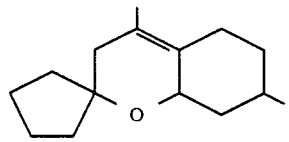

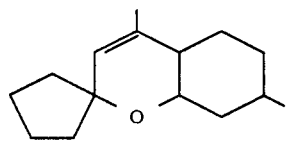

and

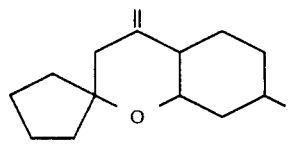

The peak indicated by reference numeral 91 is the peak for the compound having the structure:

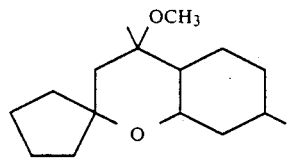

FIG. 10 is the NMR spectrum for distillation fraction 8 which contains, primarily, the compound having the structure:

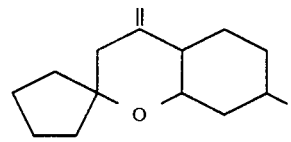

FIG. 11 is the NMR spectrum for fraction 12 of the foregoing distillation containing, primarily, the compound having the structure:

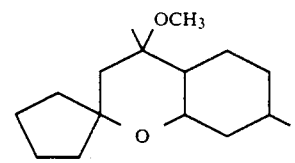

The mixture of compounds having the structures:

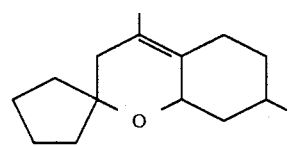

-continued

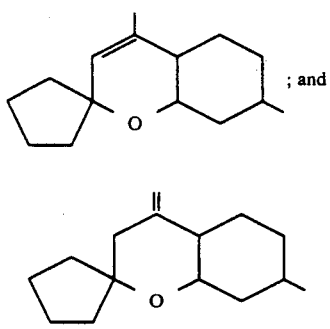
; and of distillation fraction 8 has a woody and fruity aroma profile with citrusy, minty and buttery topnotes.

The compound having the structure:

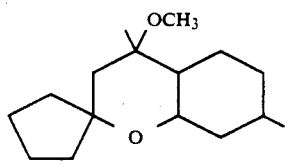

of distillation fraction 12 has a sweet and coconut aroma profile with orange peel-like topnotes.

EXAMPLE V

Reaction of Dimethyl Ketal of Acetone with Isopulegol

Reaction:

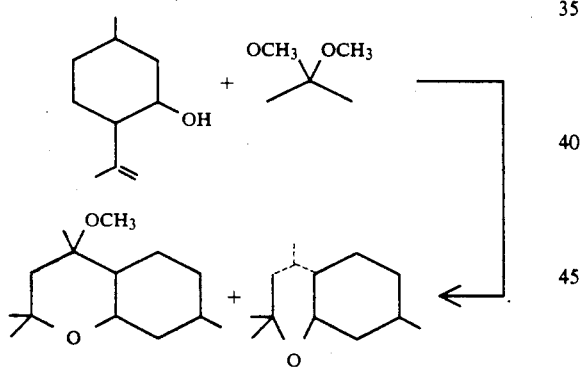

Into a 1 liter reaction vessel equipped with stirrer, thermometer, reflux condenser and heating mantle is placed 364 grams of 2,2-dimethoxy propane. The 2,2-dimethoxy propane is heated to reflux. Over a period of two hours, a pre-prepared solution of 462 grams of isopulegol and 3 grams of concentrated sulfuric acid is added to the reaction mass while refluxing same. The reaction mass is then maintained at reflux for a period of 0.5 hours after the addition of isopulegol and sulfuric acid is completed.

The reaction mass is then cooled to 50° C. and quenched with 1 liter of water. The reaction mass is then washed with 1 liter of a 10% aqueous sodium hydroxide solution.

The organic phase is separated from the aqueous phase and the organic phase is then distilled on a 1½"×15" Goodloe column yielding the following fractions:

| Fraction No. | Vapor Temp. (°C.) | Liquid Temp. (°C.) | Vacuum mm/Hg. Pressure | Reflux Ratio |
|---|---|---|---|---|
| 1 | 27/194 | 23/112 | 7.0/7.0 | 100% |
| 2 | 95 | 118 | 7.0 | 9:1 |
| 3 | 100 | 122 | 8.0 | 9:1 |
| 4 | 100 | 125 | 8.0 | 9:1 |
| 5 | 105 | 130 | 10.0 | 4:1 |
| 6 | 106 | 132 | 10.0 | 4:1 |
| 7 | 115 | 135 | 9.0 | 4:1 |
| 8 | 125 | 136 | 9.0 | 4:1 |
| 9 | 130 | 136 | 9.0 | 4:1 |
| 10 | 130 | 136 | 9.0 | 4:1 |
| 11 | 130 | 137 | 9.0 | 4:1 |
| 12 | 131 | 137 | 9.0 | 4:1 |
| 13 | 131 | 138 | 9.0 | 4:1 |
| 14 | 131 | 140 | 9.0 | 4:1 |
| 15 | 132 | 142 | 9.0 | 4:1 |
| 16 | 132 | 160 | 9.0 | 4:1 |
| 17 | 132 | 195 | 9.0 | 4:1 |
| 18 | 132 | 210 | 1.0 | 4:1. |

FIG. 12 is the GLC profile for the reaction product prior to distillation (Conditions: SE-30 column programmed at 200° C. isothermal).

The peak indicated by reference numeral 121 is the peak for the compound having the structure:

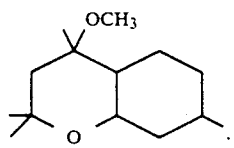

The peaks indicated by reference numerals 122, 123 and 124 are the peaks for the compounds having the structures:

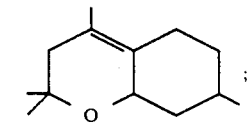

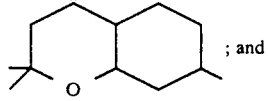
; and

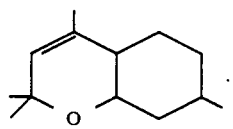

FIG. 13 is the NMR spectrum for the peak indicated by reference numeral 121 of the GLC profile of FIG. 12; for the compound having the structure:

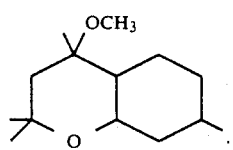

FIG. 14 is the NMR spectrum for the mixture of compounds of peaks 122, 123 and 124 of the GLC profile of FIG. 12; for the compounds having the structures:

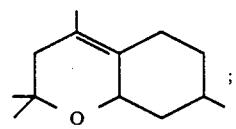

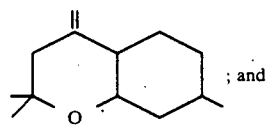
; and

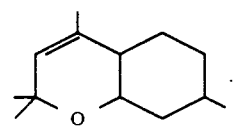

The mixture of compounds having the structures:

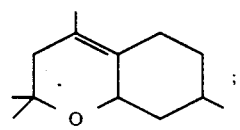
;

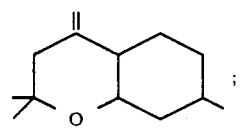
and

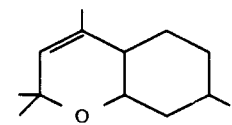

(bulked distillation fractions 2-7) has a minty, dry and woody aroma profile.

The compound having the structure:

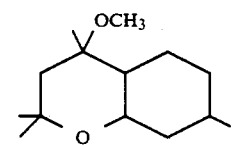

(bulked distillation fractions 11-16) has a woody, coconut-like aroma profile.

EXAMPLE VI

Reaction of Isobutyraldehyde with Isopulegol

Reaction:

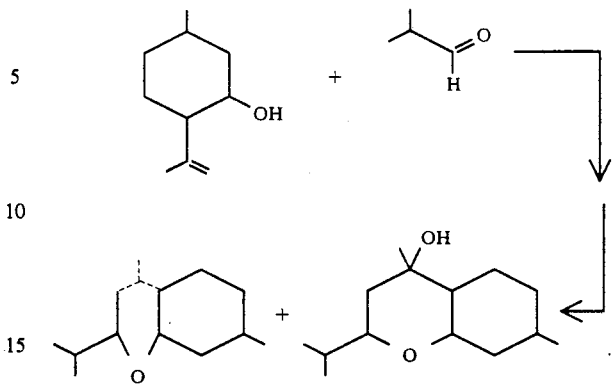

Into a 2 liter reaction vessel equipped with stirrer, thermometer, reflux condenser, heating mantle and addition funnel is placed 230 grams of isobutyraldehyde. The isobutyraldehyde is heated to reflux (68° C.). Over a period of two hours while maintaining the reaction mass at 68° C. a pre-prepared mixture of 4 grams of concentrated sulfuric acid and 500 grams of isopulegol is added dropwise to the reaction mass.

At the end of the feeding period of the isopulegol-sulfuric acid mixture, the reaction mass is heated to 85° C. and maintained at 85° C. with stirring for 0.5 hours.

The reaction mass is then quenched with 1 liter of saturated sodium carbonate solution.

The organic phase is separated from the aqueous phase and the organic phase is distilled on a 1½"×15" Goodloe column yielding the following fractions:

| Fraction No. | Vapor Temp. (°C.) | Liquid Temp. (°C.) | Vacuum mm/Hg. Pressure | Reflux Ratio |
|---|---|---|---|---|
| 1 | 23/96 | 23/125 | 10.0/5.0 | 100% |
| 2 | 96 | 125 | 3.0 | 9:1 |
| 3 | 96 | 125 | 3.0 | 9:1 |
| 4 | 100 | 135 | 3.0 | 9:1 |
| 5 | 105 | 138 | 3.0 | 9:1 |
| 6 | 108 | 138 | 3.0 | 9:1 |
| 7 | 100 | 134 | 1.0 | 9:1 |
| 8 | 100 | 134 | 1.0 | 1:1 |
| 9 | 100 | 135 | 1.0 | 1:1 |
| 10 | 100 | 135 | 1.0 | 1:1 |
| 11 | 100 | 135 | 1.0 | 1:1 |
| 12 | 100 | 140 | 1.0 | 1:1 |
| 13 | 102 | 145 | 1.0 | 1:1 |
| 14 | 100 | 185 | 1.0 | 1:1. |

FIG. 15 is the GLC profile for the reaction mass prior to distillation. (Conditions: SE-30 column programmed at 200° C. isothermal).

The peaks indicated by reference numerals 152, 153 and 154 are for the isomers of the compounds having the structure:

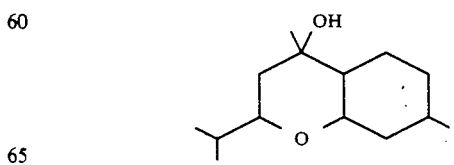

The peak indicated by reference numeral 151 is the peak for the compound having the structure:

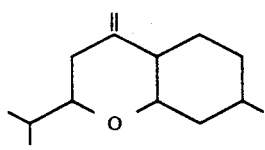

FIG. 16 is the NMR spectrum for peaks 152, 153 and 154 of the GLC profile of FIG. 15; for the compound having the structure:

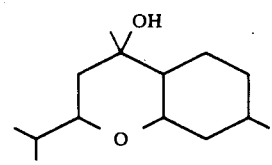

and isomers thereof.

FIG. 17 is the NMR spectrum for the peak indicated by reference numeral 151 of FIG. 15; for the compound having the structure:

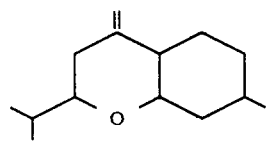

The compound having the structure:

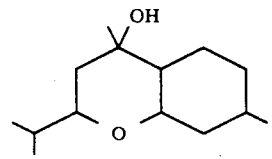

and isomers thereof (bulked distillation fractions 9–13) has a coconut-like aroma with herbaceous topnotes.

The mixture of compounds having the structures:

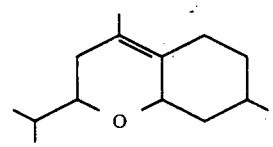

and

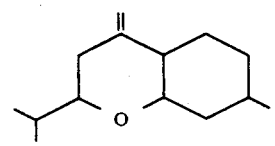

are bulked distillation fractions 4–6 has a buttery, fruity, citrusy and green aroma profile with green and coriander seed-like and fruity undertones.

EXAMPLE VII

Modified Musk Perfume Formulation

The following modified musk perfume formulations are prepared:

| Ingredients | Parts by Weight | | |
| --- | --- | --- | --- |
| | VII(A) | VII(B) | VII(C) |
| Musk Ambrette | 200 | 200 | 200 |
| Musk Ketone | 200 | 200 | 200 |
| Beta Ionone | 50 | 50 | 50 |
| Vetiveryl Acetate | 50 | 50 | 50 |
| Sandalwood Oil | 100 | 100 | 100 |
| Benzyl Benzoate | 400 | 400 | 400 |
| Mixture of compounds having the structure: <br> <br> prepared according to Example I distillation fraction 12. | 25 | 0 | 0 |
| The compound having the structure: <br> OCH$_3$ <br> prepared according to Example II distillation fraction 10. | 0 | 25 | 0 |
| Mixture of compounds having the structure: <br> <br> prepared according to Example II distillation fraction 7. | 0 | 0 | 25 |

The mixture of compounds having the structure:

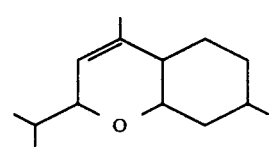

prepared according to Example I imparts to this musk formulation floral, magnolia, fruity and peach topnotes with herbaceous, peach and celery-like undertones. Accordingly, the perfume composition of Example VII(A) can be described as "a musk aroma with floral, magnolia, fruity and peach topnotes and herbaceous, peach and celery-like" undertones.

The compound having the structure:

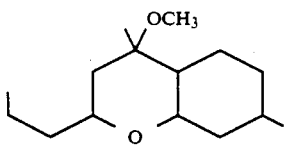

imparts to this musk perfume formulation peach and coconut undertones. Accordingly, the perfume formulation of Example VII(B) can be described as "musky with peach and coconut" undertones.

The mixture of compounds having the structure:

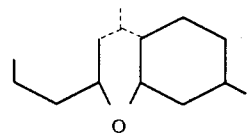

prepared according to Example II distillation fraction 7 imparts to this musky perfume formulation natural liatrix-like and hay-like undertones. Accordingly, the perfume formulation of Example VII(C) can be described as "musky with natural liatrix-like and hay-like" undertones.

EXAMPLE VIII

Preparation of Modified Musk Perfume Formulations

The following modified musk perfume formulations are prepared:

| Ingredients | Parts by Weight | | | |
|---|---|---|---|---|
| | VIII(A) | VIII(B) | VIII(C) | VIII(D) |
| Musk Ambrette | 200 | 200 | 200 | 200 |
| Musk Ketone | 200 | 200 | 200 | 200 |
| Beta Ionone | 50 | 50 | 50 | 50 |
| Vetiveryl Acetate | 50 | 50 | 50 | 50 |
| Sandalwood Oil | 100 | 100 | 100 | 100 |
| Benzyl Benzoate | 400 | 400 | 400 | 400 |
| Mixture of compounds having the structure: 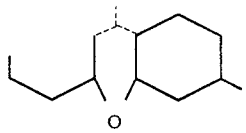 prepared according to Example II distillation fraction 1. | 25 | 0 | 0 | 0 |
| Mixture of compounds having the structure: 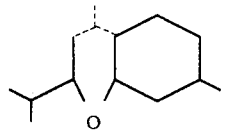 prepared according to Example III distillation fraction 7. | 0 | 25 | 0 | 0 |
| Mixture of compounds having the structure: 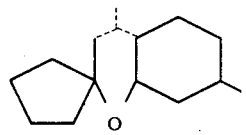 prepared according to Example IV distillation fraction 8. | 0 | 0 | 25 | 0 |
| The compound having the structure: 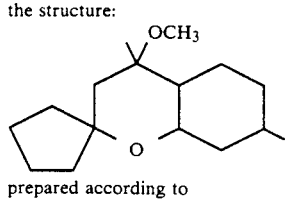 prepared according to | 0 | 0 | 0 | 25 |

The mixture of compounds defined according to the structure:

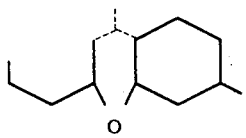

prepared according to Example II distillation fraction 1 imparts to this musk formulation sweet and coumarin-like undertones with jasmine topnotes. Accordingly, the perfume formulation of Example VIII(A) can be described as "musky with sweet and coumarinic-like undertones and jasmine" topnotes.

The mixture of compounds having the structure:

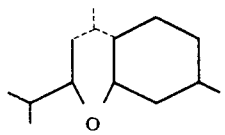

prepared to Example III imparts to this musk formulation of Example VIII(B) jasmine and lactonic undertones with jasmine and lactonic topnotes. Accordingly, the perfume formulation of Example VIII(B) can be described as "musky with jasmine and lactonic undertones and jasmine and lactonic" topnotes.

The mixture of compounds having the structure:

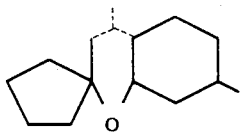

prepared according to Example IV, distillation fraction 8 imparts to this musk formulation of Example VIII(C) woody and fruity undertones with citrusy, minty and buttery topnotes. Accordingly, the perfume formulation of Example VIII(C) can be described as "musky with woody and fruity undertones and citrusy, minty and buttery" topnotes.

The compound having the structure:

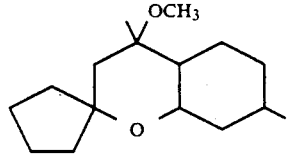

prepared according to Example IV distillation fraction 12 imparts to the musky formulation of Example VIII(D) sweet and coconut undertones and orange peel-like topnotes. Accordingly, the perfume formulation of Example VIII(D) can be described as "musky with sweet and coconut undertones with orange peel-like" topnotes.

EXAMPLE IX

Preparation of Modified Musk Perfume Formulations

The following modified musk perfume formulations are prepared:

| Ingredients | Parts by Weight | | | |
|---|---|---|---|---|
| | IX(A) | IX(B) | IX(C) | IX(D) |
| Musk Ambrette | 200 | 200 | 200 | 200 |
| Musk Ketone | 200 | 200 | 200 | 200 |
| Beta Ionone | 50 | 50 | 50 | 50 |
| Vetiveryl Acetate | 50 | 50 | 50 | 50 |
| Sandalwood Oil | 100 | 100 | 100 | 100 |
| Benzyl Benzoate | 400 | 400 | 400 | 400 |
| Mixture of compounds defined according to the structure: 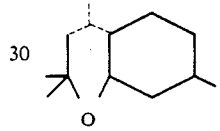 prepared according to Example V, bulked fractions 2-7. | 25 | 0 | 0 | 0 |
| The compound having the structure: 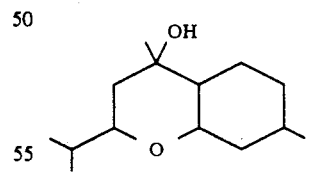 prepared according to Example V, bulked distillation fractions 11-16. | 0 | 25 | 0 | 0 |
| The compound having the structure: prepared according to Example VI, bulked distillation fractions 9-13. | 0 | 0 | 25 | 0 |
| Mixture of compounds defined according to the structure: 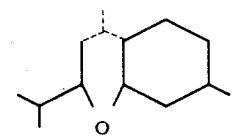 | 0 | 0 | 0 | 25 |

-continued

| Ingredients | Parts by Weight | | | |
|---|---|---|---|---|
| | IX(A) | IX(B) | IX(C) | IX(D) |
| prepared according to Example VI, bulked distillation fractions 4-6. | | | | |

The mixture of compounds defined according to the structure:

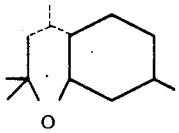

prepared according to Example V, bulked distillation fractions 2-7 imparts to this musky formulation of Example IX(A) minty, dry and woody undertones. Accordingly, the perfume formulation of Example IX(A) can be described as "musky with minty, dry and woody" undertones.

The compound having the structure:

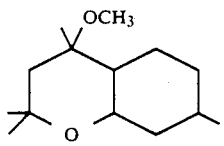

prepared according to Example V, bulked distillation fractions 11-16 imparts to this musky formulation of Example IX(B) woody and coconut-like undertones. Accordingly, the musk formulation of Example IX(B) can be described as "musky with woody and coconut-like" undertones.

The compound having the structure:

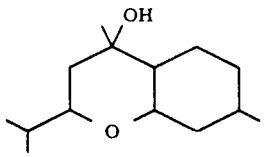

prepared according to Example VI, bulked distillation fractions 9-13 imparts to the musky perfume formulation of Example IX(C) a coconut-like undertone with herbaceous topnotes. Accordingly, the perfume formulation of Example IX(C) can be described as "musky with coconut-like undertones and herbaceous" topnotes.

The mixture of compounds having the structure:

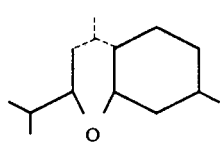

prepared according to Example VI, bulked distillation fractions 4-6 imparts to the musky formulation of Example IX(D) buttery, fruity, citrusy and green topnotes and green, coriander seed-like and fruity undertones. Accordingly, the musk formulation of Example IX(D) can be described as "musky with buttery, fruity, citrusy and green topnotes and green, coriander seed-like and fruity" undertones.

EXAMPLE X

Preparation of a Soap Composition

100 Grams of soap chips are admixed with 1 gram of one of the perfume substances of Table II below until a substantially homogeneous composition is obtained. The perfumed soap manifests an excellent aroma as set forth in Table II below.

TABLE II

| Perfume Ingredients | Aroma |
|---|---|
| Mixture of compounds having the structure:  prepared according to Example I, distillation fraction 12. | A floral, magnolia, fruity and peach aroma profile with herbaceous, peach and celery-like undertones. |
| The compound having the structure:  prepared according to Example II distillation fraction 10. | A peach and coconut aroma profile. |
| Mixture of compounds having the structure:  prepared according to Example II distillation fraction 1. | A sweet and coumarin-like aroma with jasmine topnotes. |
| Mixture of compounds having the structure:  prepared according to Example II distillation fraction 7. | A natural, liatrix-like and hay-like aroma profile. |
| Mixture of compounds having the structure:  prepared according to Example III distillation fraction 7. | A jasmine, lactonic aroma with jasmine and lactonic undertones. |

TABLE II-continued

| Perfume Ingredients | Aroma |
|---|---|
| Mixture of compounds having the structure: 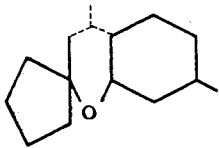 prepared according to Example IV distillation fraction 8. | A woody and fruity aroma profile with citrusy, minty and buttery topnotes. |
| The compound having the structure: 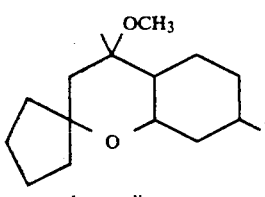 prepared according to Example IV distillation fraction 12. | A sweet and coconut aroma profile with orange peel-like topnotes. |
| Mixture of compounds having the structure: 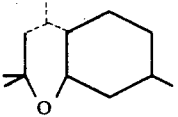 prepared according to Example V, bulked distillation fractions 2-7. | A minty, dry and woody aroma profile. |
| The compound having the structure: 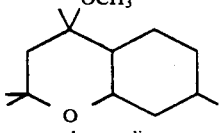 prepared according to Example V, bulked distillation fractions 11-16. | A woody and coconut-like aroma profile. |
| The compound having the structure: 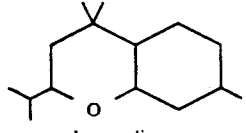 prepared according to Example VI, bulked distillation fractions 9-13. | A coconut-like aroma with herbaceous topnotes. |
| Mixture of compounds having the structure: 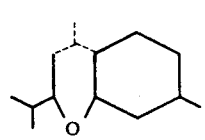 prepared according to Example VI, bulked distillation fractions 4-6. | A buttery, fruity, citrusy and green aroma profile with green, coriander seed-like and fruity undertones. |
| Perfume composition of Example VII(A). | A musk aroma with floral, magnolia, fruity and peach topnotes and herbaceous, peach and celery-like undertones. |
| Perfume composition of Example VII(B). | Musky, with peach and coconut undertones. |
| Perfume composition of Example VII(C). | Musky, with natural liatrix-like and hay-like undertones. |
| Perfume composition of Example VIII(A). | Musky, with sweet and coumarinic-like undertones and jasmine topnotes. |
| Perfume composition of Example VIII(B). | Musky, with jasmine and lactonic undertones and jasmine and lactonic topnotes. |
| Perfume composition of Example VIII(C) | Musky, with woody and fruity undertones and citrusy, minty and buttery topnotes. |
| Perfume composition of Example VIII(D). | Musky, with sweet and coconut undertones with orange peel-like topnotes. |
| Perfume composition of Example IX(A). | Musky, with minty, dry and woody undertones. |
| Perfume composition of Example IX(B). | Musky, with woody and coconut-like undertones. |
| Perfume composition of Example IX(C). | Musky, with coconut-like undertones and herbaceous topnotes. |
| Perfume composition of Example IX(D). | Musky, with buttery, fruity, citrusy and green topnotes and green, coriander seed-like and fruity undertones. |

EXAMPLE XI

Preparation of a Cologne and Handkerchief Perfume

One of the perfume substances are set forth in Table II of Example X is incorporated into a cologne at concentrations of 1.5%, 2.0%, 2.5%, 3.0%, 3.5% and 4.0% in 80%, 85%, 90% and 95% aqueous ethanol; and into handkerchief perfumes at concentrations of 15%, 20%, 25% and 30% (in 85%, 90% and 95% aqueous ethanol). Distinct and definite fragrances as set forth in Table II of Example X are imparted to the cologne and to the handkerchief perfume at each of the levels indicated.

EXAMPLE XII

Preparation of a Cosmetic Powder Composition

A cosmetic powder is prepared by mixing in a ball mill, 100 grams of talcum powder with 0.15 grams of one of the substances of Table II of Example X. The resulting powders have excellent sweet musk aromas.

EXAMPLE XIII

Utilizing the procedure of Example I of column 15 of U.S. Pat. No. 3,632,396 the specification for which is incorporated by reference herein, a non-woven cloth substrate useful as a drier-added fabric-softening article of manufacture is prepared wherein the substrate, the substrate coating and the outer coating and the perfuming material are as follows:

1. a water "dissolvable" paper ("Dissolvo Paper");
2. Adogen 448 (m.p. about 140° F.) as the substrate coating; and
3. an outer coating having the following formulation (m.p. about 150° F.);
   - 57 percent $C_{20-22}$HAPS
   - 27 percent isopropyl alcohol
   - 20 percent antistatic agent 1 percent of one of the perfume substances of Table II of Example X.

Fabric-softening compositions prepared as set forth above having an aroma characteristic as set forth in Table II of Example X essentially consists of a substrate having a weight of about 3 grams per 100 square inches, a substrate coating of about 1.85 grams per 100 square inches of substrate and an outer coating of about 1.4 grams per 100 square inches of substrate thereby providing a total aromatized substrate and an outer coating weight ratio of about 1:1 by weight of the substrate. Aromas are imparted as set forth in Table II of Example X in a pleasant manner to the head space in the dryer on operation thereof using the said dryer added fabric softening non-woven fabric.

EXAMPLE XIV

Preparation of a Soap Composition

100 Grams of soap chips are prepared according to Example V of U.S. Pat. No. 4,058,490 issued on Nov. 15, 1977 the specification for which is incorporated herein by reference, as follows:

"The sodium salt of an equal mixture of $C_{10}$–$C_{14}$ alkane sulfonates (95% active), 40 lbs. is dissolved in a mixture of 80 lbs of anhydrous isopropanol and 125 lbs. of deionized water at 150° F. In this mixture is dissolved 10 lbs. of partially hydrogenated coconut oil fatty acids and 15 lbs. of sodium mono-$C_{14}$-alkyl maleate, and the pH of this solution is adjusted to 6.0 by the addition of a small amount of a 50% aqueous solution of NaOH. The isopropanol is distilled off and the remaining aqueous solution is dried. The resulting solid actives are then blended in a chip mixer with 10 lbs. water 0.2 lb. titanium hydroxide."

The resulting blend is then mixed with one of the perfume substances of Table II of Example X until a substantially homogeneous composition is obtained. The perfumed soap composition manifests an aroma as set forth in Table II of Example X.

EXAMPLE XV

Granular Detergent Composition

A granular detergent composition is prepared according to United Kingdom Patent No. 1,501,498 the specification for which is incorporated by reference herein having the following formula. It is prepared by spray-drying the following mixture:

| Ingredient | Parts by Weight |
| --- | --- |
| Sodium salt of ethoxylated fatty alcohol sulfate having an average of about 2.25 moles of ethylene oxide per mole of fatty alcohol | 14.1 |
| Sodium tallow alkyl sulfate | 2.4 |
| Sodium silicate solids ratio: $SiO_2/Na_2O = 2.0$ | 6.0 |
| Sodium tripolyphosphate | 24.0 |
| $Na_{12}(AlO_2.SiO_2).27H_2O$ | 18.0 |
| Moisture | 10.0 |
| Sodium sulfate | 25.0 |
| Perfume substance of Table II of Example X | 4.0 |

Laundry solutions containing the above detergent compositions are used to launder fabrics. Each of the laundry compositions both prior to and on laundering give rise to a pleasant aroma as set forth in Table II of Example X.

EXAMPLE XVI

Perfumed Liquid Detergent

Concentrated liquid detergents are prepared with aromas as set forth in Table II of Example X containing 0.10%, 0.15% and 0.20% of each of the substances of Table II of Example X in the liquid detergent. The liquid detergent is a builder free liquid detergent consisting of (a) 50% of a nonionic surfactant having an HLB of 8.0 and a critical micelle concentration of 0.007 weight percent at 25° C.; (b) an anionic surfactant which is a triethanolamine prepared according to United Kingdom Patent No. 1,491,603 the specification for which is incorporated by reference herein.

The detergents all possess aromas as set forth in Table II of Example X, supra.

EXAMPLE XVII

Preparation of a Detergent Composition

A total of 100 grams of detergent powder (a low phosphate content detergent composition which contains 12% by weight phosphate builder, 8 percent hardness mineral ion insensitive detergent, 0.9 percent by weight maleic anhydride-vinyl compound co-polymer and 2 percent alkylene oxide condensation product prepared according to Example IV at column IX, U.S. Pat. No. 4,000,080 issued on Dec. 28, 1976, the specification for which is incorporated by reference herein) is intimately admixed with 0.15 grams of one of the perfume materials of Table II of Example X, supra, until a substantially homogeneous composition is obtained. The composition has an aroma as set forth in Table II of Example X, supra.

EXAMPLE XVIII

Each of the fragranced materials of Table II of Example X, supra, are added to a 50:50 weight:weight mixture of low density polyethylene:polyepsilon caprolactone PCL-700 forming pellets with scents as set forth in Table II of Example X, supra.

75 Pounds of a mixture of PCL-700 polyepsilon caprolactone (manufactured by the Union Carbide Corporation of New York, N.Y. having a melting point of about 180°-190° F.): Low density polyethylene are heated to about 250° C. in a container of the kind illustrated in FIGS. 18 and 19. 25 Pounds of each of the fragrance materials as set forth in Table II of Example X is then quickly added to the liquified polymer mixture, the lid 228 is put in place and the agitating means 273 are actuated. The temperature is then raised to about 260° F. and the mixing is continued for 5-15 minutes. The valve "V" is then opened to allow flow of the molten polymer enriched with perfume ingredient to exit through the orifices 234. The liquid falling through the orifices 234 solidified almost instantaneously upon impact with the moving cooled conveyer 238. Polymer beads or pellets 244 having pronounced scents as described in Table II of Example X, supra, are thus formed. Analysis demonstrates that the pellets contain about 25% of the perfume material so that almost no losses in the scenting substance did occur. These pellets may be called "master pellets".

50 Pounds of each batch of the scent containing "master pellets" are then added to one thousand pounds of unscented polypropylene and the mass is heated to the liquid state. The liquid is molded into thin sheets of films. The thin sheets of films have pronounced aromas as set forth in Table II of Example X, supra. The sheets of films are cut into strips of 0.25" in width×3" in length and placed into room air fresheners.

On operation of the room air freshener, after four minutes, the room in each case has an aesthetically pleasing aroma with no foul odor being present, the aroma being described in Table II of Example X, supra.

What is claimed is:

1. A process for augmenting or enhancing the aroma of a perfume composition, cologne or perfumed article comprising the step of adding to a perfume composition, cologne or perfumed article, an aroma augmenting or enhancing quantity of a mixture of alkyl substituted tetra- or hexahydrobenzopyran derivatives defined according to the structure:

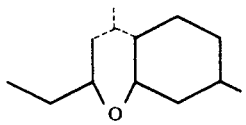

wherein in each of the compounds of the mixture one of the dashed lines is a carbon-carbon double bond and each of the other of the dashed lines is a carbon-carbon single bond.

2. A process for augmenting or enhancing the aroma of a perfume composition, cologne or perfumed article comprising the step of adding to a perfume composition, cologne or perfumed article, an aroma augmenting or enhancing quantity of the compound defined according to the structure:

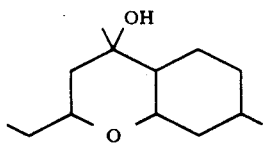

3. A process for augmenting or enhancing the aroma of a perfume composition, cologne or perfumed article comprising the step of adding to a perfume composition, cologne or perfumed article, an aroma augmenting or enhancing quantity of the compound defined according to the structure:

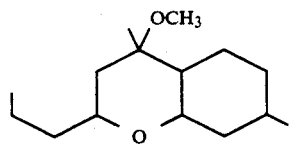

4. A process for augmenting or enhancing the aroma of a perfume composition, cologne or perfumed article comprising the step of adding to a perfume composition, cologne or perfumed article, an aroma augmenting or enhancing quantity of the compound defined according to the structure:

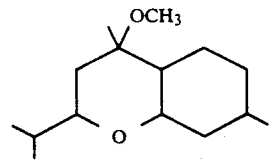

5. A process for augmenting or enhancing the aroma of a perfume composition, cologne or perfumed article comprising the step of adding to a perfume composition, cologne or perfumed article, an aroma augmenting or enhancing quantity of the compound defined according to the structure:

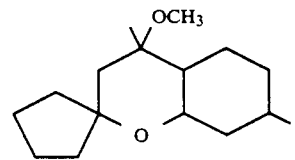

6. A process for augmenting or enhancing the aroma of a perfume composition, cologne or perfumed article comprising the step of adding to a perfume composition, cologne or perfumed article, an aroma augmenting or enhancing quantity of the compound defined according to the structure:

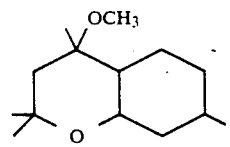

7. A process for augmenting or enhancing the aroma of a perfume composition, cologne or perfumed article comprising the step of adding to a perfume composition, cologne or perfumed article, an aroma augmenting or enhancing quantity of the compound defined according to the structure:

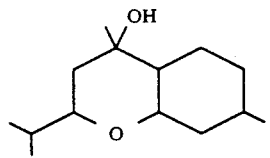

8. A process for augmenting or enhancing the aroma of a perfume composition, cologne or perfumed article comprising the step of adding to a perfume composition, cologne or perfumed article, an aroma augmenting or enhancing quantity of at least one alkyl substituted tetra- or hexahydrobenzopyran derivative defined according to the structure:

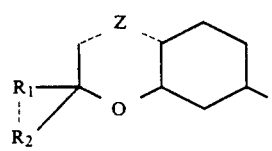

wherein Z is a moiety selected from the group consisting of:

wherein in the moiety:
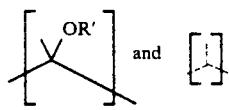 and 
one of the dashed lines represents a carbon-carbon double bond and each of the other of the dashed lines represent carbon-carbon single bonds; wherein R' is hydrogen, methyl or ethyl; wherein $R_1$ and $R_2$ taken separately are the same or different hydrogen or $C_1$–$C_3$ alkyl or $R_1$ and $R_2$ taken together complete a $C_5$–$C_6$ cycloalkyl moiety.
* * * * *